US012364718B2

(12) United States Patent
Zimmerman et al.

(10) Patent No.: US 12,364,718 B2
(45) Date of Patent: Jul. 22, 2025

(54) MICROBIAL COMPOSITIONS TO INCREASE THE PRODUCTION OF PCA FROM POLYPHENOLS

(71) Applicant: Church & Dwight Co., Inc., Princeton, NJ (US)

(72) Inventors: Noah Paul Zimmerman, Chapel Hill, NC (US); Alexandra Helena Smith, Greendale, WI (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 17/401,792

(22) Filed: Aug. 13, 2021

(65) Prior Publication Data

US 2022/0047650 A1 Feb. 17, 2022

Related U.S. Application Data

(60) Provisional application No. 63/065,739, filed on Aug. 14, 2020.

(51) Int. Cl.
*A61K 35/742* (2015.01)
*C12N 1/20* (2006.01)
*C12R 1/125* (2006.01)

(52) U.S. Cl.
CPC .............. *A61K 35/742* (2013.01); *C12N 1/20* (2013.01); *C12R 2001/125* (2021.05)

(58) Field of Classification Search
CPC ..................... A61K 35/742; C12N 1/20; C12R 2001/125
See application file for complete search history.

(56) References Cited

U.S. PATENT DOCUMENTS

| 9,585,925 B1 | 3/2017 | Bascharon |
| 2004/0076614 A1 | 4/2004 | Schur |
| 2010/0233312 A9 | 9/2010 | Stojanovic |
| 2017/0173091 A1 | 6/2017 | Lynch |

FOREIGN PATENT DOCUMENTS

| CN | 105748610 | 7/2016 |
| CN | 107509839 | 12/2017 |
| CN | 108902487 A | 11/2018 |
| CN | 109549000 A | 4/2019 |
| CN | 109997958 A | 7/2019 |
| EP | 1171103 | 12/2004 |
| JP | 4260597 | 4/2009 |
| KR | 101274333 | 6/2013 |
| KR | 2013 0114942 A | 10/2013 |
| KR | 20160079269 | 7/2016 |
| KR | 20170142518 | 12/2017 |

OTHER PUBLICATIONS

Thomas, T.M., and Walker, J.R.L. "Metabolism of Quercetin by a *Penicillium* Sp." New Zealand Natural Sciences, vol. 20 (1993): 63-70. (Year: 1993).*
Hirooka, Kazutake, and Yasutaro Fujita. "Excess Production of Bacillus Subtilis Quercetin 2,3-Dioxygenase Affects Cell Viability in the Presence of Quercetin." Bioscience, biotechnology, and biochemistry 74.5 (2010): 1030-1038. Web. (Year: 2010).*
Dabeek WM, Marra MV. Dietary Quercetin and Kaempferol: Bioavailability and Potential Cardiovascular-Related Bioactivity in Humans. Nutrients. Sep. 25, 2019;11(10):2288. doi: 10.3390/nu11102288. PMID: 31557798; PMCID: PMC6835347. (Year: 2019).*
Helmann JD. Purification of Bacillus subtilis RNA polymerase and associated factors. Methods Enzymol. 2003;370:10-24. doi: 10.1016/S0076-6879(03)70002-0. PMID: 14712630. (Year: 2003).*
Klayraung S, Viernstein H, Okonogi S. Development of tablets containing probiotics: Effects of formulation and processing parameters on bacterial viability. Int J Pharm. Mar. 31, 2009;370(1-2):54-60. doi: 10.1016/j.ijpharm.2008.11.004. Epub Nov. 18, 2008. PMID: 19059323. (Year: 2009).*
Tan IS, Ramamurthi KS. Spore formation in Bacillus subtilis. Environ Microbiol Rep. Jun. 2014;6(3):212-25. doi: 10.1111/1758-2229.12130. Epub Dec. 17, 2013. PMID: 24983526; PMCID: PMC4078662. (Year: 2014).*
Schaab, M. R., et al., Kinetic and spectroscopic studies on the quercetin 2,3-dioxygenase from Bacillus subtilis, Biochemistry. Jan. 24, 2006;45(3): 1009-16. US.
Stevens, J.F., et al., The Chemistry of Gut Microbial Metabolism of Polyphenols, Phytochem. Rev. (Jun. 2016), 15(3): 425-444. US https://www.ncbi.nlm.nih.gov/pmc/articles/PMC4888912/.
Dudonne, S., et al., Modulatory effects of a cranberry extract co-supplementation with Bacillus subtilis CU1 probiotic on phenolic compounds bioavailability and gut microbiota compoisition in high-fat diet-fed mice, PharmaNutrition (2015), vol. 3 (3), pp. 89-100 US.
Rhayat, L., et al., "Effect of *Bacillus subtilis* Strains on Intestinal Barrier Function and Inflammatory Response," *Frontiers In Immunology*, 2019, vol. 10(Article 564), pp. 1-10.

* cited by examiner

*Primary Examiner* — Louise W Humphrey
*Assistant Examiner* — John Paul Selwanes
(74) *Attorney, Agent, or Firm* — Church & Dwight Co., Inc.

(57) ABSTRACT

Compositions and methods for converting at least one polyphenol to protocatechuic acid (PCA) using *Bacillus subtilis* 1579, or active variants thereof, are provided. Conversion of polyphenols, such as quercetin, to PCA can decrease inflammation, decrease cortisol levels, and increase milk quality and milk production quantity in milk-producing agricultural animals. Accordingly, provided herein are compositions comprising *B. subtilis* 1579, or an active variant thereof, for administration to humans for decreasing inflammation or for administration to milk-producing agricultural animals for decreasing inflammation, decreasing cortisol levels, and increasing milk quality and milk production.

6 Claims, 16 Drawing Sheets
Specification includes a Sequence Listing.

ANTIMICROBICS

| Abbr. | Name |
|---|---|
| TGC | Tigecycline |
| TET | Tetracycline |
| CHL | Chloramphenicol |
| DAP | Daptomycin |
| STR | Streptomycin |
| TYLT | Tylosin tartrate |
| SYN | Quinupristin / dalfopristin |
| LZD | Linezolid |
| NIT | Nitrofurantoin |
| PEN | Penicillin |
| KAN | Kanamycin |
| ERY | Erythromycin |
| CIP | Ciprofloxacin |
| VAN | Vancomycin |
| LIN | Lincomycin |
| GEN | Gentamicin |
| POS | Positive Control |
| NEG | Negative Control |

|   | 1 | 2 | 3 | 4 | 5 | 6 | 7 | 8 | 9 | 10 | 11 | 12 |
|---|---|---|---|---|---|---|---|---|---|---|---|---|
| A | TGC 0.015 | TGC 0.03 | TGC 0.06 | TGC 0.12 | TGC 0.25 | TGC 0.5 | ERY 0.25 | ERY 0.5 | ERY 1 | ERY 2 | ERY 4 | ERY 8 |
| B | TET 1 | TET 2 | TET 4 | TET 8 | TET 16 | TET 32 | CIP 0.12 | CIP 0.25 | CIP 0.5 | CIP 1 | CIP 2 | CIP 4 |
| C | CHL 2 | CHL 4 | CHL 8 | CHL 16 | CHL 32 | PEN 0.25 | PEN 0.5 | PEN 1 | PEN 2 | PEN 4 | PEN 8 | PEN 16 |
| D | DAP 0.25 | DAP 0.5 | DAP 1 | DAP 2 | DAP 4 | DAP 8 | DAP 16 | VAN 0.25 | VAN 0.5 | VAN 1 | VAN 2 | VAN 4 |
| E | STR 512 | STR 1024 | STR 2048 | NIT 2 | NIT 4 | NIT 8 | NIT 16 | NIT 32 | NIT 64 | VAN 8 | VAN 16 | VAN 32 |
| F | TYLT 0.25 | TYLT 0.5 | TYLT 1 | TYLT 2 | TYLT 4 | TYLT 8 | TYLT 16 | TYLT 32 | GEN 128 | GEN 256 | GEN 512 | GEN 1024 |
| G | SYN 0.5 | SYN 1 | SYN 2 | SYN 4 | SYN 8 | SYN 16 | SYN 32 | LIN 1 | LIN 2 | LIN 4 | LIN 8 | NEG |
| H | LZD 0.5 | LZD 1 | LZD 2 | LZD 4 | LZD 8 | KAN 128 | KAN 256 | KAN 512 | KAN 1024 | POS | POS | POS |

FIG. 3

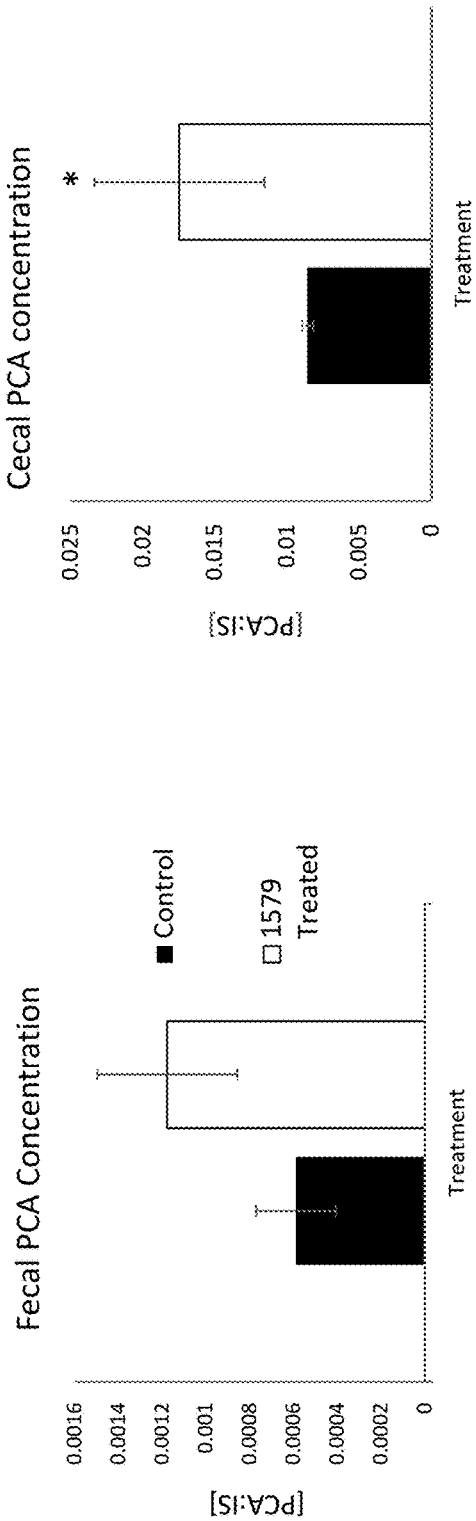
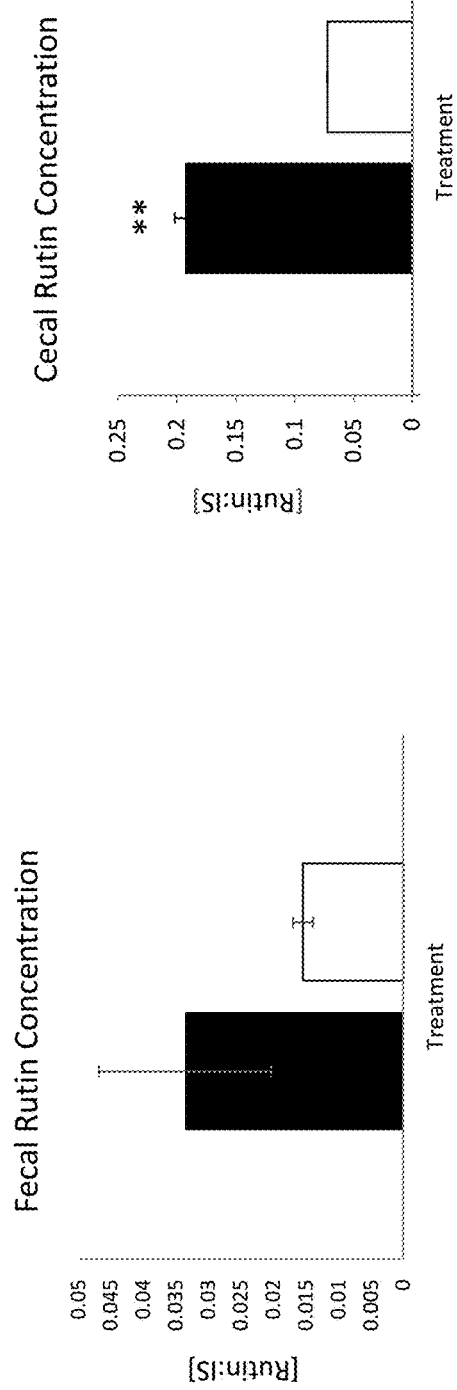
FIG. 4A
FIG. 4B
FIG. 4C
FIG. 4D

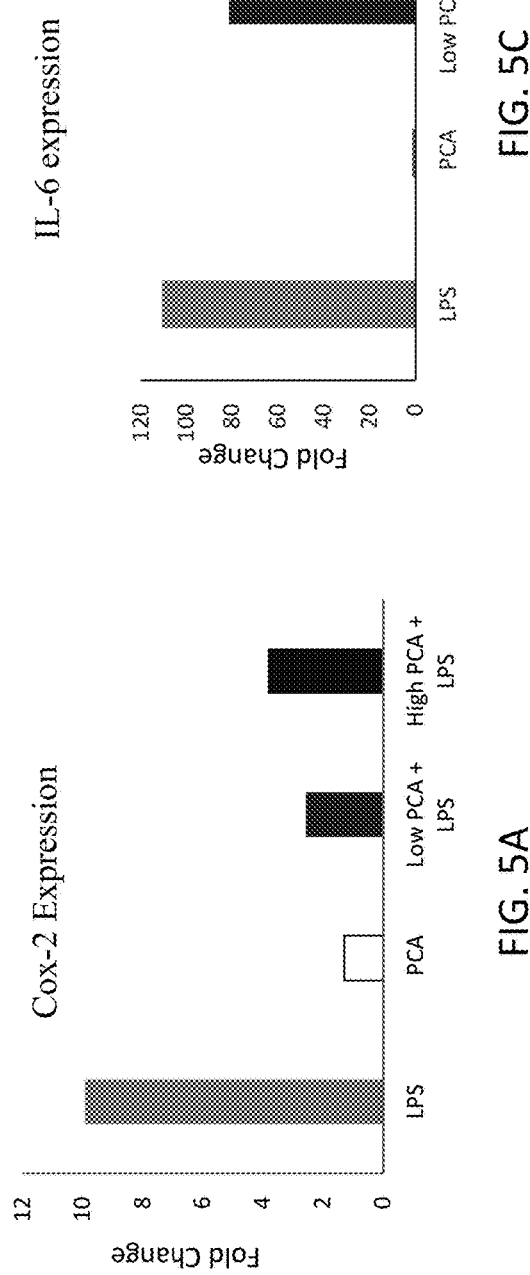
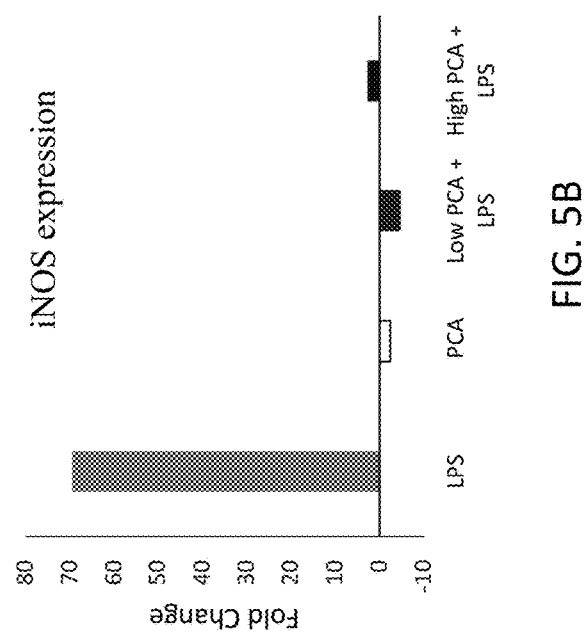
FIG. 5A
FIG. 5B
FIG. 5C

```
                        SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: primer QDOIB

<400> SEQUENCE: 1
ttgggatcct tatggtttca tcacc                                          25

<210> SEQ ID NO 2
<211> LENGTH: 22
<212> TYPE: DNA
<213> ORGANISM: Artificial Sequence
<220> FEATURE:
<223> OTHER INFORMATION: primer QDOIN

<400> SEQUENCE: 2
gatcatatga aaacattatg ta                                             22

<210> SEQ ID NO 3
<211> LENGTH: 20
<212> TYPE: DNA
<213> ORGANISM: Artificial Sequence
<220> FEATURE:
<223> OTHER INFORMATION: AGAGTTTGATYMTGGCTCAG

<400> SEQUENCE: 3
agagtttgat ymtggctcag                                                20

<210> SEQ ID NO 4
<211> LENGTH: 16
<212> TYPE: DNA
```

<213> ORGANISM: Artificial Sequence
<220> FEATURE:
<223> OTHER INFORMATION: primer 1492R-Y

<400> SEQUENCE: 4
taccttgtta ygactt                                                        16

<210> SEQ ID NO 5
<211> LENGTH: 1014
<212> TYPE: DNA
<213> ORGANISM: Bacillus subtilis
<220> FEATURE:
<223> OTHER INFORMATION: Quercetin 2,3-dioxygenase

<400> SEQUENCE: 5
atgaaaacat tatgtacaca ttcattgcct aaagataaaa tgccttattt gctccggagc        60
ggagaaggcg agcgctatct gttcggcaga caggttgcca cggtgatggc gaatgggagg       120
agcacaggtg atttgtttga gatcgtgctt ctttccgggg gaaaaggaga tgcctttccg       180
cttcacgtcc acaaggacac acatgaagga attctcgttt ggacgggaaa actggaactg       240
acacttgatg gtgaacgcta tttattaata tcaggtgatt atgcgaacat tccggcggga       300
acaccgcaca gctaccggat gcagagccac agaacaagac tggtatctta cacgatgaaa       360
ggaaacgtag cgcacttgta ttccgttatt gggaatccgt atgatcacgc tgaacatccg       420
ccgtacgcaa gcgaagaagt ctcaaacgag cgatttgcag aagcagccgc tgtagcggac       480
attgtatttc tagatgaagg aaagcctgca tgttcggcca aattagcgga acttacagag       540
ctgccagatg gagcggttcc atacgttctt gaatctggag aaggagatcg cctgttgact       600
ggagatcagc ttcaccgcat tgtggctgca caaaaaaata cagatggcca gtttatcgtc       660
gtatcctctg aaggccctaa aggtgaccga atcgttgatc actaccatga acatcataca       720
gaaacatttt attgccttga aggtcagatg acgatgtggg cagatggcca ggaaattcag       780
ctgaatccgg gagatttcct gcatgtccct gcaaataccg ttcactccta tcgccttgat       840
tcttactata caaagatggt gggcgtattg gttcctggtt tatttgaacc gttttttccgg       900 acgttaggcg acccgtatga aggccacatc ttcccatgtg agcctcaggc tttgcacttt       960
gatcgcgttt tgcagaatat cgaagcatta gatttaaagg tgatgaaacc ataa            1014

<210> SEQ ID NO 6
<211> LENGTH: 337
<212> TYPE: PRT
<213> ORGANISM: Bacillus subtilis
<220> FEATURE:
<223> OTHER INFORMATION: Quercetin 2,3-dioxygenase

<400> SEQUENCE: 6

Met Lys Thr Leu Cys Thr His Ser Leu Pro Lys Asp Lys Met Pro Tyr
1               5                   10                  15

Leu Leu Arg Ser Gly Glu Gly Glu Arg Tyr Leu Phe Gly Arg Gln Val
            20                  25                  30

Ala Thr Val Met Ala Asn Gly Arg Ser Thr Gly Asp Leu Phe Glu Ile
        35                  40                  45

Val Leu Leu Ser Gly Gly Lys Gly Asp Ala Phe Pro Leu His Val His
    50                  55                  60

Lys Asp Thr His Glu Gly Ile Leu Val Leu Asp Gly Lys Leu Glu Leu
65                  70                  75                  80

Thr Leu Asp Gly Glu Arg Tyr Leu Leu Ile Ser Gly Asp Tyr Ala Asn
                85                  90                  95

```
Ile Pro Ala Gly Thr Pro His Ser Tyr Arg Met Gln Ser His Arg Thr
            100                 105                 110
Arg Leu Val Ser Tyr Thr Met Lys Gly Asn Val Ala His Leu Tyr Ser
        115                 120                 125
Val Ile Gly Asn Pro Tyr Asp His Ala Glu His Pro Pro Tyr Ala Ser
130                 135                 140
Glu Glu Val Ser Asn Glu Arg Phe Ala Glu Ala Ala Val Ala Asp
145                 150                 155                 160
Ile Val Phe Leu Asp Glu Gly Lys Pro Ala Cys Ser Ala Lys Leu Ala
                165                 170                 175
Glu Leu Thr Glu Leu Pro Asp Gly Ala Val Pro Tyr Val Leu Glu Ser
            180                 185                 190
Gly Glu Gly Asp Arg Leu Leu Thr Gly Asp Gln Leu His Arg Ile Val
        195                 200                 205
Ala Ala Gln Lys Asn Thr Asp Gly Gln Phe Ile Val Ser Ser Glu
    210                 215                 220
Gly Pro Lys Gly Asp Arg Ile Val Asp His Tyr His Glu His Thr
225                 230                 235                 240
Glu Thr Phe Tyr Cys Leu Glu Gly Gln Met Thr Met Trp Ala Asp Gly
                245                 250                 255
Gln Glu Ile Gln Leu Asn Pro Gly Asp Phe Leu His Val Pro Ala Asn
            260                 265                 270
Thr Val His Ser Tyr Arg Leu Asp Ser Tyr Tyr Thr Lys Met Val Gly
        275                 280                 285
Val Leu Val Pro Gly Leu Phe Glu Pro Phe Phe Arg Thr Leu Gly Asp
    290                 295                 300
Pro Tyr Glu Gly His Ile Phe Pro Cys Glu Pro Gln Ala Leu His Phe
305                 310                 315                 320
Asp Arg Val Leu Gln Asn Ile Glu Ala Leu Asp Leu Lys Val Met Lys
                325                 330                 335
Pro

<210> SEQ ID NO 7
<211> LENGTH: 22
<212> TYPE: DNA
<213> ORGANISM: Artificial Sequence
<220> FEATURE:
<223> OTHER INFORMATION: primer iNOSF

<400> SEQUENCE: 7
ggctacggaa ctggacatca ac                                              22

<210> SEQ ID NO 8
<211> LENGTH: 19
<212> TYPE: DNA
<213> ORGANISM: Artificial Sequence
<220> FEATURE:
<223> OTHER INFORMATION: primer iNOSR

<400> SEQUENCE: 8
ctcagggatt ctggagacg                                                  19

<210> SEQ ID NO 9
<211> LENGTH: 21
<212> TYPE: DNA
```

```
<213> ORGANISM: Artificial Sequence
<220> FEATURE:
<223> OTHER INFORMATION: primer COX2F

<400> SEQUENCE: 9
tcctgaaacc cactcccaac a                                              21

<210> SEQ ID NO 10
<211> LENGTH: 20
<212> TYPE: DNA
<213> ORGANISM: Artificial Sequence
<220> FEATURE:
<223> OTHER INFORMATION: primer COX2R

<400> SEQUENCE: 10
tgggcagtca tcaggcacag                                                20

<210> SEQ ID NO 11
<211> LENGTH: 22
<212> TYPE: DNA
<213> ORGANISM: Artificial Sequence
<220> FEATURE:
<223> OTHER INFORMATION: primer IL6F

<400> SEQUENCE: 11
atgacttctg ctttccctac cc                                             22

<210> SEQ ID NO 12
<211> LENGTH: 22
<212> TYPE: DNA
<213> ORGANISM: Artificial Sequence
<220> FEATURE:
<223> OTHER INFORMATION: primer IL6R

<400> SEQUENCE: 12
gctgctttca cactcatcat tc                                             22

<210> SEQ ID NO 13
<211> LENGTH: 22
<212> TYPE: DNA
<213> ORGANISM: Artificial Sequence
<220> FEATURE:
<223> OTHER INFORMATION: primer GAPDH-F

<400> SEQUENCE: 13
gtcttcacta ccatggagaa gg                                             22

<210> SEQ ID NO 14
<211> LENGTH: 20
<212> TYPE: DNA
<213> ORGANISM: Artificial Sequence
<220> FEATURE:
<223> OTHER INFORMATION: primer GAPDH-R

<400> SEQUENCE: 14
tcatggatga ccttggccag                                                20
```

MICROBIAL COMPOSITIONS TO INCREASE THE PRODUCTION OF PCA FROM POLYPHENOLS

CROSS-REFERENCE TO RELATED APPLICATIONS

This application claims priority from U.S. Provisional Application No. 63/065,739, filed Aug. 14, 2020, which application is hereby incorporated in its entirety by reference in this application.

FIELD OF THE INVENTION

The present invention relates to microbial compositions for increasing the production of protocatechuic acid from polyphenols.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of C63806_1530US_SL.txt, a creation date of Oct. 21, 2021 and a size of 6.9 KB. The sequence listing filed via EFS-Web is part of the specification and is hereby incorporated in its entirety by reference herein.

BACKGROUND OF THE INVENTION

Bioavailability is a key criterion for many therapeutic compounds to have efficacy. While dietary polyphenols are linked to improvements against degenerative diseases such as cardiovascular diseases, neurodegenerative diseases and cancer, the greatest problem facing the efficacy of dietary polyphenols in disease prevention is their poor bioavailability (Cerda et al., 2005; Manach et al., 2005a). Although polyphenols in plants show great anti-inflammatory and antioxidant potential their absorption into the body and tissue distribution is low (Cerda et al., 2003; Keppler and Humpf, 2005) and the tissue distribution of polyphenols is not always proportional to the oral dose (Boer et al., 2005), which constrains the perceived functionality and efficacy within a population. Microbial metabolites of polyphenols are more bioavailable (Cerda et al., 2004; Larrosa et al., 2009; Seeram et al., 2006) and often more beneficial than the parent compound (Kay et al., 2009; Larrosa et al., 2009; Masella et al., 2012; Núñez-Sánchez et al., 2016; Vicinanza et al., 2013; Yuan et al., 2016). Human intervention studies have indicated that the production of specific polyphenol metabolites is linked with a reduced risk of disease such as prostate and breast cancer (Atkinson et al., 2005; Núñez-Sánchez et al., 2016). Consistent with this, in both a colitis model, as well as in human fibroblasts, a phenolic metabolite was more effective than the parent compound at inhibiting inflammation (Giménez-Bastida et al., 2012; Larrosa et al., 2010) and operate through well-known signaling pathways. For instance, compounds such as quercetin and anthocyanins are not as well absorbed or bioavailable as the metabolite protocatechuic acid (Tsuda et al., 1999).

Protocatechuic acid (PCA) has great capacity to prevent or modulate a large spectrum of diseases based on the ability to inhibit inflammatory pathways, regulate cell proliferation and regulate antioxidant pathways. Recent research has demonstrated the ability of protocatechuic acid to inhibit inflammatory cytokine and lipid pathways (Min et al., 2010; Peiffer et al., 2016; Wang et al., 2010), modulate atherosclerotic lesions (Masella et al., 2004) through antioxidant enzyme expression, and the ability to interfere with cancer development and metastasis (Lin et al., 2011; Peiffer et al., 2016; Yin et al., 2009). However, the levels of PCA commonly ingested in the diet of animals and humans are relatively low. In contrast, compounds such as anthocyanins and quercetin are found in higher concentrations in mammalian diets (Manach et al., 2005b; Sampson et al., 2002) and can then be metabolized to PCA through specific bacterial degradation, if the required bacteria are present.

The supplementation of exogenous or chemically synthesized protocatechuic acid may provide some health benefit however, added cost, dosing restrictions and the added potential of losing efficacy to continued breakdown of PCA during storage and in the gastrointestinal tract provide barriers to utility. Probiotics or direct-fed microbials are a viable alternative given the advancement of the science in recent years and acceptable costs of the products for commercial use. Functioning as protocatechuic acid factories, specific probiotic strains of bacteria allow for the production of PCA as metabolites from dietary sources, increasing the efficiency of dietary utilization. Accordingly, there is a recognized need for products and methods to efficiently produce anti-inflammatory, chemopreventive, antioxidant compounds from dietary sources to enhance health and disease prevention.

BRIEF SUMMARY OF THE INVENTION

Compositions and methods for converting at least one polyphenol to protocatechuic acid (PCA) using *Bacillus subtilis* 1579, or active variants thereof, are provided. Conversion of polyphenols, such as quercetin, to PCA can decrease inflammation, decrease cortisol levels, and increase milk quality and milk production quantity in milk-producing agricultural animals. Accordingly, provided herein are compositions comprising *B. subtilis* 1579, or an active variant thereof, for administration to humans for decreasing inflammation or for administration to milk-producing agricultural animals for decreasing inflammation, decreasing cortisol levels, and increasing milk quality and milk production.

Embodiment 1. A bacterial strain composition comprising:
(a) *Bacillus subtilis* 1579, or an active variant of any thereof; and/or
(b) at least one of a spore, or a forespore, or a combination of cells, forespores and/or spores of *Bacillus subtilis* 1579, or an active variant of any thereof;
wherein said *Bacillus subtilis* 1579, spore, or a forespore, or a combination of cells, forespores and/or spores or the active variant of any thereof is present at about $10^5$ CFU/gram to about $10^{12}$ CFU/gram or at about $10^5$ CFU/ml to about $10^{12}$ CFU/ml.

Embodiment 2. The bacterial strain composition of embodiment 1, wherein an effective amount of said bacterial strain composition increases conversion of at least one polyphenol to protocatechuic acid (PCA).

Embodiment 3. The bacterial strain composition of embodiment 1, wherein said at least one polyphenol comprises a flavonoid polyphenol.

Embodiment 4. The bacterial strain composition of embodiment 3, wherein said flavonoid polyphenol comprises quercetin, apigenin, luteolin, anthocyanin, and/or rutin. Additionally, or alternatively, said flavonoid polyphenol comprises quercetin glycoside, apigenin glycoside, luteolin glycoside, anthocyanin glycoside, and/or rutin glycoside.

Embodiment 5. The bacterial strain composition of embodiment 1, wherein said composition comprises a cell paste or lyophilized powder.

Embodiment 6. The bacterial strain composition of embodiment 1, wherein said *Bacillus subtilis* 1579 is deposited under accession number NRRL B-67952.

Embodiment 7. The composition of embodiment 2, wherein administration of said effective amount of said bacterial strain composition decreases the expression of a marker of inflammation compared to a proper control.

Embodiment 8. The composition of embodiment 7, wherein the marker of inflammation comprises Cox-2, iNOS, and/or IL-6.

Embodiment 9. The composition of embodiment 2, wherein cortisol levels are decreased in a subject following administration of said effective amount of said bacterial strain composition. The cortisol levels can be plasma cortisol level from a blood sample taken from a milk-producing animal, such as a human or a cow, to which the bacterial strain composition is administered.

Embodiment 10. The composition of embodiment 2, wherein administration of said effective amount of said bacterial strain composition to a milk-producing agricultural animal decreases body weight loss, increases a marker of milk quality, and/or increases levels of milk. The decrease in body weight loss can be a decrease of at least 10% or a decrease of at least 50 lb. The increase in a marker of milk quality can be an increase of at least 10% in milk protein level, lactose content, or milkfat level. The increase in the level of milk can be an increase of at least 10%.

Embodiment 11. An animal feed product comprising the composition of any one of embodiment 1-10. The animal feed product can further comprise at least one polyphenol. For example, the animal feed product can further comprise quercetin, apigenin, rutin, anthocyanin, and/or luteolin. Additionally, or alternatively, the animal feed product can further comprise quercetin glycoside, apigenin glycoside, and/or luteolin glycoside.

Embodiment 12. A method of increasing the production of protocatechuic acid (PCA) from at least one polyphenol, said method comprising combining said at least one polyphenol with an effective amount of a bacterial strain composition comprising:
a) *Bacillus subtilis* 1579, or an active variant of any thereof; and/or
b) at least one of a spore, or a forespore, or a combination of cells, forespores and/or spores of *Bacillus subtilis* 1579, or an active variant of any thereof,
wherein said effective amount of said bacterial strain composition comprises about $10^5$ CFU/gram to about $10^{12}$ CFU/gram or at about $10^5$ CFU/ml to about $10^{12}$ CFU/ml. The method can be performed in vitro on bovine endothelial cells or in vivo in a human subject or agricultural animal, such as a milk-producing ruminant.

Embodiment 13. The method of embodiment 12, wherein said at least one polyphenol comprises a flavonoid polyphenol.

Embodiment 14. The method of embodiment 12, wherein said flavonoid polyphenol comprises quercetin, apigenin, luteolin, and/or rutin.

Embodiment 15. The method of embodiment 12, wherein production of PCA is increased by at least about 10% compared to the level of PCA produced in an appropriate control.

Embodiment 16. A method of decreasing inflammation in a subject, said method comprising administering an effective amount of a bacterial strain composition to said subject, said bacterial strain composition comprising:
a) *Bacillus subtilis* 1579, or an active variant of any thereof; and/or
b) at least one of a spore, or a forespore, or a combination of cells, forespores and/or spores of *Bacillus subtilis* 1579, or an active variant of any thereof. The administration can be a single administration or multiple doses.

Embodiment 17. The method of embodiment 16, wherein said subject is a human or agricultural animal.

Embodiment 18. The method of embodiment 16, wherein said decrease in inflammation comprises a decrease in the expression of at least one of Cox-2, iNOS, and/or IL-6.

Embodiment 19. A method of decreasing cortisol levels in a subject, said method comprising administering an effective amount of a bacterial strain composition to said subject, said bacterial strain composition comprising:
a) *Bacillus subtilis* 1579, or an active variant of any thereof; and/or
b) at least one of a spore, or a forespore, or a combination of cells, forespores and/or spores of *Bacillus subtilis* 1579, or an active variant of any thereof. The administration can be a single administration or multiple doses. Cortisol levels can be measured in a blood sample taken from a milk-producing ruminant.

Embodiment 20. The method of embodiment 19, wherein said subject is a human or agricultural animal.

Embodiment 21. A method of increasing the quality or amount of milk produced from an agricultural animal, said method comprising administering an effective amount of a bacterial strain composition to said milk-producing agricultural animal, said bacterial strain composition comprising:
a) *Bacillus subtilis* 1579, or an active variant of any thereof; and/or
b) at least one of a spore, or a forespore, or a combination of cells, forespores and/or spores of *Bacillus subtilis* 1579, or an active variant of any thereof, wherein said effective amount of said bacterial strain composition comprises about $10^5$ CFU/gram to about $10^{12}$ CFU/gram or at about $10^5$ CFU/ml to about $10^{12}$ CFU/ml. The administration can be a single administration or multiple doses. The administration can further comprise feeding at least one polyphenol. For example, administering can further comprise feeding quercetin, apigenin, and/or luteolin.

Embodiment 22. The method of embodiment 21, wherein increasing the quality of milk produced from an agricultural animal comprises an increase in milkfat, an increase in milk protein, and/or an increase in the lactose content produced by said milk-producing agricultural animal. The increase in milkfat can be an increase of at least 10%. The increase in milk protein can be an increase of at least 10% of casein. The increase in lactose content can be an increase of at least 10%.

Embodiment 23. The method of embodiment 21, wherein said administration of an effective amount of a bacterial strain composition decreases body weight loss by said milk producing agricultural animal when compared to a control milk-producing animal that was not administered an effective amount of said bacterial strain composition. The decrease in body weight loss can be a decrease of at least 10% or a decrease of 50lb.

Embodiment 24. The method of embodiment 21, wherein said administering comprises feeding said milk-producing agricultural animal an animal feed comprising said effective amount of said bacterial strain composition. The administering can be by top dress or liquid drench.

Embodiment 25. The method of any one of embodiment 12-24, wherein said *Bacillus subtilis* 1579 is deposited under accession number NRRL B-67952.

Embodiment 26. Use of the composition of any one of embodiments 1-11 for the treatment of an inflammatory disorder in a human subject.

Embodiment 27. Use of the composition of any one of embodiments 1-11 for the manufacture of a medicament for useful for treating an inflammatory disorder in a human subject.

BRIEF DESCRIPTION OF THE DRAWINGS

FIG. 3 presents a layout of the 96-well microliter plate (CMV3AGPF) used for measuring resistance of *B. subtilis* 1579 to selected antimicrobials. The value listed in each box is the concentration of the indicated antimicrobial agent in μg/mL.

FIGS. 4A-4D show the PCA and rutin concentrations in feces and cecum of mice fed 0.1% polyphenol diet. FIG. 4A is a graph showing PCA concentration in feces of mice fed with 0.1% polyphenol diet. FIG. 4B is a graph showing PCA concentration in cecum of mice fed with 0.1% polyphenol diet. FIG. 4C is a graph showing rutin concentration in feces of mice fed with 0.1% polyphenol diet. FIG. 4D is a graph showing rutin concentration in cecum of mice fed with 0.1% polyphenol diet. * $p<0.05$ (significant difference from control), ** $p<0.005$ (significant difference from control)

FIGS. 5A-5C depict expression of inflammatory marker genes in bovine endothelial cells during LPS stimulation with and without protocatechuic acid (PCA) treatment. FIG. 5A is a graph showing expression of Cox-2 in bovine endothelial cells during LPS stimulation with and without PCA treatment. FIG. 5B is a graph showing expression of iNOS in bovine endothelial cells during LPS stimulation with and without PCA treatment. FIG. 5C is a graph showing expression of IL-6 in bovine endothelial cells during LPS stimulation with and without PCA treatment.

FIG. 7A is a chromatograph showing PCA production in Participant #1 at day 0. FIG. 7B is a chromatograph showing PCA production in Participant #1 at day 10. FIG. 7C is a chromatograph showing PCA production in Participant #3 at day 0. FIG. 7D is a chromatograph showing PCA production in Participant #3 at day 10. FIG. 7E is a chromatograph showing PCA production in Participant #5 at day 0. FIG. 7F is a chromatograph showing PCA production in Participant #5 at day 10. FIG. 7G is a chromatograph showing PCA standard.

FIG. 9A is a graph showing bovine cortisol levels at day 0 (control) or 7 days after treatment with *B. subtilis* 1579 on a high quercetin diet. FIG. 9B is a graph showing weight loss in tie stalls with and without treatment with *B. subtilis* 1579.

FIG. 10A is a graph comparing total milk production per week in untreated control cows and cows treated with *B. subtilis* 1579 (* $p<0.03$). FIG. 10B is a graph comparing total milk production per day in untreated control cows and cows treated with *B. subtilis* 1579. FIG. 10C is a graph comparing percentage of milk butter fat in milk from untreated control cows and cows treated with *B. subtilis* 1579 (* $p<0.05$). FIG. 10D is a graph comparing percent milk protein in milk from untreated control cows and cows treated with *B. subtilis* 1579. FIG. 10E is a graph comparing percent lactose in milk from untreated control cows and cows treated with *B. subtilis* 1579.

DETAILED DESCRIPTION

Figure 1:
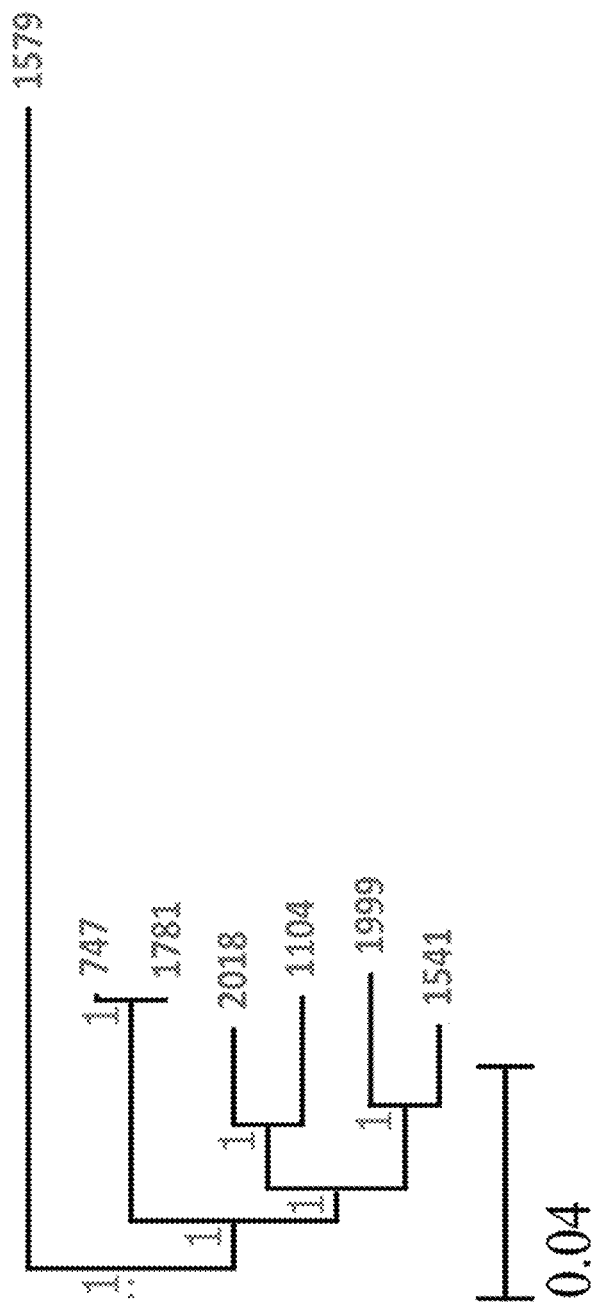
FIG. 1 reports the whole genome phylogenetic tree indicating the relatedness of similar *Bacillus* strains to each other on the basis of whole genome comparison.

The present disclosure now will be described more fully hereinafter. The disclosure may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural references unless the context clearly dictates otherwise.

I. Overview

Compositions and methods for converting at least one polyphenol to protocatechuic acid using *Bacillus subtilis* 1579 are provided. A bacterial composition, bacterial strain, modified bacterial strain, microbial strain, microbial composition, or modified microbial strain or active variant thereof are used herein to describe a microorganism that is used to convert at least one polyphenol to PCA. Conversion of polyphenols, such as quercetin, to PCA can decrease inflammation, decrease cortisol levels, and increase milk quality and milk production quantity in milk-producing agricultural animals.

Phenolic acids, such as PCA, can exert protective and anti-inflammatory effects by scavenging free radicals and directly binding cellular targets that can inhibit inflammatory enzymes and modulate cellular receptors leading to regulation of growth and immune responses. According to the methods and compositions disclosed herein any precursor polyphenol can be used as a substrate for PCA production by *B. subtilis* 1579.

As used herein the term "polyphenol" denotes a structural class of mainly natural, but also synthetic or semisynthetic, organic chemicals characterized by the presence of multiples of phenol structural units. The number and characteristics of these phenol structures underlie the unique physical, chemical, and biological properties (e.g., metabolic, toxic, therapeutic, etc.). Examples include (but not limited to) quercetin, anthocyanins, curcumin (curcuminoids), resveratrol, luteolin, polydatin, silymarin, silibinin, tannic acid, epigallocatechin gallate (EGCG), and ellagitannin. The general physical properties include water-insoluble, moderately water-insoluble and moderately water-soluble compounds with molecular weight of 500-4000 Da, >12 phenolic hydroxyl groups, and 5-7 aromatic rings per 1000 Da (these are general ranges and may be.+−0.20% and be within the definition of polyphenol. Examples of polyphenol include but are not limited to and include derivatives thereof: quercetin, trans-resveratrol, curcumin, silymarin (standardized Milk Thistle extract), and epigallocatechin gallate (EGCG—standardized Green Tea extract). In specific embodiments, the polyphenols used for conversion to PCA include flavonoid polyphenols. Examples of flavonoid polyphenols include, but are not limited to quercetin (also known as 2-(3,4-dihydroxyphenyl)-3,5,7-trihydroxy-4H-chromen-4-one; 5,7,3',4'-flavon-3-ol; Sophoretin; Meletin; Quercetine; Xanthaurine; Quercetol; Quercitin; Quertine; and Flavin meletin), quercetin glucosides, rutin (also known as 2-(3,4-dihydroxyphenyl)-5,7-dihydroxy-3-[α-L-rhamnopyranosyl-(1→6)-β-D-glucopyranosyloxy]-4H-chromen-4-one; 2-(3,4-dihydroxyphenyl)-5,7-dihydroxy-3-{[(2S,3R,4S,5S,6R)-3,4,5-trihydroxy-6-({[(2R,3R,4R,5R,6S)-3,4,5-trihydroxy-6-methyloxan-2-yl]oxy}methyl)oxan-2-yl]oxy}-4H-chromen-4-one; Rutoside (INN); Phytomelin; Sophorin; Birutan; Eldrin; Birutan Forte; Rutin trihydrate; Globularicitrin; Violaquercitrin; and Quercetin rutinoside), flavonoid apigenin (also known as 5,7-Dihydroxy-2-(4-hydroxyphenyl)-4H-1-benzopyran-4-one; Apigenine; Chamomile; Apigenol; Spigenin; Versulin; 4',5,7-Trihydroxyflavone; and C.I. Natural Yellow 1), luteolin (also known as 2-(3,4-Dihydroxyphenyl)-5,7-dihydroxy-4-chromenone; Luteolol; Digitoflavone; Flacitran; Luteoline; and 3',4',5,7-Tetrahydroxyflavone), cyanidin (also known as 2-(3,4-Dihydroxyphenyl)chromenylium-3,5,7-triol), kaempferol (also known as 3,5,7-Trihydroxy-2-(4-hydroxyphenyl)-4H-chromen-4-one; 3,5,7-trihydroxy-2-(4-hydroxyphenyl)-4H-1-benzopyran-4-one; Kaempherol; Robigenin; Pelargidenolon; Rhamnolutein; Rhamnolutin; Populnetin; Trifolitin; Kempferol; and Swartziol), myricetin (also known as 3,5,7-Trihydroxy-2-(3,4,5-trihydroxyphenyl)-4-chromenone; Cannabiscetin; Myricetol; and Myricitin), daidzein (also known as 7-Hydroxy-3-(4-hydroxyphenyl) chromen-4-one; 4',7-Dihydroxyisoflavone; Daidzeol; and Isoaurostatin), genistein (also known as 5,7-Dihydroxy-3-(4-hydroxyphenyl)chromen-4-one; and 4',5,7-Trihydroxyisoflavone), catechins (also known as (2R,3S)-2-(3,4-Dihydroxyphenyl)-3,4-dihydro-2H-chromene-3,5,7-triol; Cianidanol; (+)-catechin; D-Catechin; Catechinic acid; Catechuic acid; Cianidol; Dexcyanidanol; (2R,3S)-Catechin; 2,3-trans-Catechin; and (2R,3S)-Flavan-3,3',4',5,7-pentol), gallocatechins (also known as Gallocatechol), naringin (also known as 7-[[2-O-(6-Deoxy-α-L-mannopyranosyl)-β-D-glucopyranosyl]oxy]-2,3-dihydro-5-hydroxy-2-(4-hydroxyphenyl)-4H-1-benzopyran-4-one; Naringin; Naringoside; 4',5,7-Trihydroxyflavanone-7-rhamnoglucoside; and Naringenin 7-O-neohesperidoside), hesperitin (also known as (S)-2,3-Dihydro-5,7-dihydroxy-2-(3-hydroxy-4-methoxyphenyl)-4H-1-benzopyran-4-one), anthocyanins, and combinations thereof. Examples of flavonoid polyphenols may also include quercetin glycosides, quercetin glucosides, rutin glycosides, apigenin glycosides, luteolin glycosides, anthocyanin glycosides, cyanidin glucoside (also known as cyanin), and combinations thereof.

As used herein the term "Quercetin" denotes a flavonoid widely distributed in nature and is the aglycone form of a number of other flavonoid glycosides, such as rutin and quercetin, found in citrus fruit, buckwheat and onions. Quercetin is a polyphenolic flavonoid with potential chemopreventive activity. Quercetin, ubiquitous in plant food sources and a major bioflavonoid in the human diet, may produce antiproliferative effects resulting from the modulation of either EGFR or estrogen-receptor mediated signal transduction pathways. Although the mechanism of action is not fully known, the following effects have been described with this agent in vitro: decreased expression of mutant p53 protein and p21-ras oncogene, induction of cell cycle arrest at the G1 phase and inhibition of heat shock protein synthesis. Quercetin can also produce anti-inflammatory and anti-allergy effects mediated through the inhibition of the lipoxygenase and cyclooxygenase pathways, thereby preventing the production of pro-inflammatory mediators.

In some embodiments, the polyphenols used for conversion to PCA are found in natural or dietary sources. For example, quercetin used for conversion to PCA can be found in natural sources including many fruits, vegetables, leaves, and grains commonly known in the art. Alternatively, processed sources of quercetin can be used for conversion including natural extracts and dietary supplements.

II. Bacterial Strains

Compositions and methods comprising *Bacillus subtilis* 1579 are provided which can be used to convert polyphenolic compounds to PCA. Cell populations comprising *B. subtilis* 1579 are provided, as well as populations of spores derived from *B. subtilis* 1579, or any preparation thereof. Thus, various bacterial strain compositions and/or the feed compositions provided herein comprise as an active ingredient a cell population comprising *B. subtilis* 1579, or an active variant thereof.

*B. subtilis* 1579 was deposited with the Patent Depository of the National Center for Agricultural Utilization Research Agricultural Research Service, U.S. Department of Agriculture, 1815 North University Street, Peoria, Illinois 61604 U.S.A. on 13, Apr. 2020 and assigned deposit No. NRRL B-67952. The deposit identified above will be maintained under the terms of the Budapest Treaty on the International Recognition of the Deposit of Microorganisms for the Purposes of Patent Procedure. The deposit of *B. subtilis* 1579 was made merely as a convenience for those of skill in the art and is not an admission that a deposit is required under 35 U.S.C. § 112.

The term "isolated" encompasses a bacterium, spore, or other entity or substance, that has been (1) separated from at least some of the components with which it was associated when initially produced (whether in nature or in an experimental setting), and/or (2) produced, prepared, purified, and/or manufactured by the hand of man. Isolated bacteria may be separated from at least about 10%, about 20%, about 30%, about 40%, about 50%, about 60%, about 70%, about 80%, about 90%, or more of the other components with which they were initially associated.

As used herein, a substance is "pure" if it is substantially free of other components. The terms "purify," "purifying" and "purified" refer to a bacterium, spore, or other material that has been separated from at least some of the components with which it was associated either when initially produced or generated (e.g., whether in nature or in an experimental setting), or during any time after its initial production. A bacterium or spore or a bacterial population or a spore population may be considered purified if it is isolated at or after production, such as from a material or environment containing the bacterium or bacterial population or spore, and a purified bacterium or bacterial population or spore may contain other materials up to about 10%, about 20%, about 30%, about 40%, about 50%, about 60%, about 70%, about 80%, about 90%, or above about 90% and still be considered purified. In some embodiments, purified bacteria or spores and bacterial populations or spore populations are more than about 80%, about 85%, about 90%, about 91%, about 92%, about 93%, about 94%, about 95%, about 96%, about 97%, about 98%, about 99%, or more than about 99% pure. In specific embodiments, a culture of bacteria contains no other bacterial species in quantities to be detected by normal bacteriological techniques.

By "population" is intended a group or collection that comprises two or more (i.e., 10, 100, 1,000, 10,000, $1\times10^6$, $1\times10^7$, or $1\times10^8$ or greater). Various compositions are provided herein that comprise a population of *B. subtilis* 1579 or an active variant thereof. In specific embodiments, the population of at least one of a bacterial strain (i.e., *B. subtilis* 1579 or an active variant thereof, or spores or forespores or a combination of cells, forespores and/or spores, formed from *B. subtilis* 1579, or an active variant thereof) comprises a concentration of at least about $10^5$ CFU/ml to about $10^{11}$ CFU/ml, about $10^5$ CFU/ml to about $10^{10}$ CFU/ml, about $10^5$ CFU/ml to about $10^{12}$ CFU/ml, about $10^5$ CFU/ml to about $10^6$ CFU/ml, about $10^6$ CFU/ml to about $10^7$ CFU/ml, about $10^7$ CFU/ml to about $10^8$ CFU/ml, about $10^8$ CFU/ml to about $10^9$ CFU/ml, about $10^9$ CFU/ml to about $10^{10}$ CFU/ml, about $10^{10}$ CFU/ml to about $10^{11}$ CFU/ml, about $10^{11}$ CFU/ml to about $10^{12}$ CFU/ml. In other embodiments, the concentration of the bacterial strain provided herein or active variant thereof comprises at least about $10^5$ CFU/ml, at least about $10^6$ CFU/ml, at least about $10^7$ CFU/ml, at least about $10^8$ CFU/ml, at least about $10^9$ CFU/ml, at least about $10^{10}$ CFU/ml, at least about $10^{11}$ CFU/ml, or at least about $10^{12}$ CFU/ml.

In specific embodiments, the population of at least one of a bacterial strain (i.e., *B. subtilis* 1579 or an active variant thereof, or spores or forespores or a combination of cells, forespores and/or spores, formed from *B. subtilis* 1579, or an active variant thereof) comprises a concentration of at least about $10^5$ CFU/g to about $10^{11}$ CFU/g, about $10^5$ CFU/g to about $10^{10}$ CFU/g, about $10^5$ CFU/g to about $10^{12}$ CFU/g, about $10^5$ CFU/g to about $10^6$ CFU/g, about $10^6$ CFU/g to about $10^7$ CFU/g, about $10^7$ CFU/g to about $10^8$ CFU/g, about $10^8$ CFU/g to about $10^9$ CFU/g, about $10^9$ CFU/g to about $10^{10}$ CFU/g, about $10^{10}$ CFU/g to about $10^{11}$ CFU/g, about $10^{11}$ CFU/g to about $10^{12}$ CFU/g. In other embodiments, the concentration of the bacterial strain provided herein or active variant thereof comprises at least about $10^5$ CFU/g, at least about $10^6$ CFU/g, at least about $10^7$ CFU/g, at least about $10^8$ CFU/g, at least about $10^9$ CFU/g, at least about $10^{10}$ CFU/g, at least about $10^{11}$ CFU/g, or at least about $10^{12}$ CFU/g.

A "spore" refers to at least one dormant (at application) but viable reproductive unit of a bacterial species. Non-limiting methods by which spores are formed from *B. subtilis* 1579 (or variants thereof) are disclosed elsewhere herein. It is further recognized the populations disclosed herein can comprise a combination of vegetative cells and forepores (cells in an intermediate stage of spore formation); a combination of forespores and spores; or a combination of forespores, vegetative cells, and/or spores. In specific embodiments the *B. subtilis* 1579 (or variant thereof) is a viable cell, spore, or forespore.

A. Formulations of *Bacillus subtilis* 1579

The compositions comprising a bacterial strain (i.e., *B. subtilis* 1579, or an active variant thereof, or a spore or a forespore or a combination of cells, forespores or/and spores, from *B. subtilis* 1579, or an active variant thereof) can further comprise at least one or more of an extender, a solvent, spontaneity promoters, carriers, emulsifiers, dispersants, frost protectants, thickeners, and/or adjuvants. Examples of typical formulations include top dress, liquid drench, water-soluble liquids (SL), emulsifiable concentrates (EC), emulsions in water (EW), suspension concentrates (SC, SE, FS, OD), water-dispersible granules (WG), granules (GR) and capsule concentrates (CS); WG; GR; BB; SG; ZC.

The carrier combined with *B. subtilis* 1579 can be selected based on the intended use of the final bacterial strain composition. In some embodiments, the bacterial strain composition is intended for administration to an agricultural animal, such as a milk-producing agricultural animal. Thus, the bacterial strain composition may be presented in various physical forms, for example, as a top dress, as a water soluble concentrate for use as a liquid drench or to be added to a milk replacer, gelatin capsule, granule, or gels. In specific embodiments of the top dress form, a freeze-dried bacterial strain composition is added to a carrier, such as whey, maltodextrin, sucrose, dextrose, limestone (calcium carbonate), rice hulls, yeast culture, dried starch, and/or sodium silico aluminate. Alternatively, a spray-dried bacterial strain composition can be added to a carrier, such as whey, maltodextrin, sucrose, dextrose, limestone (calcium carbonate), rice hulls, yeast culture, dried starch, and/or sodium silico aluminate. Further examples of formulations for the bacterial strain composition include water-soluble liquids, emulsifiable concentrates, emulsions in water, suspension concentrates, water-dispersible granules, granules, and capsule concentrates.

In one embodiment the bacterial strain composition is provided as a water soluble concentrate for a liquid drench or milk replacer supplement. In such embodiments freeze-dried bacterial strain can be added to a water soluble carrier, such as whey, maltodextrin, sucrose, dextrose, dried starch, sodium silico aluminate, and a liquid is added to form the drench or the supplement is added to milk or a milk replacer. In one embodiment the bacterial strain composition is provided as a gelatin capsule form, wherein freeze-dried bacterial strain can be added to a carrier, such as whey, maltodextrin, sugar, limestone (calcium carbonate), rice hulls, yeast culture dried starch, and/or sodium silico aluminate. In one embodiment, the bacteria and carrier are enclosed in a degradable gelatin capsule. In one embodiment the bacterial strain composition is provided as a gel form, wherein freeze-dried bacterial strain is added to a carrier, such as vegetable oil, sucrose, silicon dioxide, polysorbate 80, propylene glycol, butylated hydroxyanisole, citric acid, ethoxyquin, and/or artificial coloring to form the gel.

The bacterial strain compositions may be admixed with a dry formulation of additives including but not limited to growth substrates, enzymes, sugars, carbohydrates, extracts and growth promoting micro-ingredients. The sugars could include the following: lactose; maltose; dextrose; maltodextrin; glucose; fructose; mannose; tagatose; sorbose; raffinose; and galactose.

The sugars range from 50-95%, either individually or in combination. The extracts could include yeast or dried yeast fermentation solubles ranging from 5-50%. The growth substrates could include: trypticase, ranging from 5-25%; sodium lactate, ranging from 5-30%; and, Tween 80, ranging from 1-5%. The carbohydrates could include mannitol, sorbitol, adonitol and arabitol.

The carbohydrates range from 5-50% individually or in combination. The micro-ingredients could include the following: calcium carbonate, ranging from 0.5-5.0%; calcium chloride, ranging from 0.5-5.0%; dipotassium phosphate, ranging from 0.5-5.0%; calcium phosphate, ranging from 0.5-5.0%; manganese proteinate, ranging from 0.25-1.00%; and, manganese, ranging from 0.25-1.0%.

In specific embodiments, the bacterial strain compositions may be mixed with polyphenols, artificial polyphenol preparations, or natural products containing polyphenols for conversion to PCA. In specific embodiments, the bacterial strain compositions disclosed herein are combined with vegetable or forage products high in quercetin levels in order to increase the amount of PCA delivered to a subject. The bacterial strain compositions disclosed herein can be combined with a prebiotic selected to enhance the growth or activity of *B. subtilis* 1579. For example, the prebiotic can be inulin, fructo-oligosaccharides, or galacto-oligosaccharides.

Provided herein are animal feed compositions formulated with the bacterial strain compositions comprising *B. subtilis* 1579. Animal feed compositions can be prepared by adding any bacterial strain composition described herein and carrier(s) (where used) to a ribbon or paddle mixer and mixed for about 15 minutes, although the timing can be increased or decreased. The components can be blended such that a uniform mixture of the cultures and carriers result. The final product can be a dry, flowable powder. The bacterial strain compositions disclosed herein can then be added to animal feed or a feed premix, added to an animal's water, or administered in other ways known in the art. In particular embodiments, any feed for an animal can be supplemented with one or more bacterial strain compositions comprising *B. subtilis* 1579 described herein. In specific embodiments, the bacterial strain compositions disclosed herein are formulated in animal feed with quercetin, apigenein, and/or luteolin. The concentration of quercetin, apigenein, and/or luteolin can individually be about 1-50 ug/g feed, about 1-40 ug/g feed, about 2-8 ug/g feed, about 8-12 ug/g feed, about 30-40 ug/g feed or 33-38 ug/g feed, about 3 ug/g feed, about 4 ug/g feed, about 5 ug/g feed, about 6 ug/g feed, about 7 ug/g feed, about 8 ug/g feed, about 9 ug/g feed, about 10 ug/g feed, about 11 ug/g feed, about 12 ug/g feed, about 30 ug/g feed, about 31 ug/g feed, about 32 ug/g feed, about 33 ug/g feed, about 34 ug/g feed, about 35 ug/g feed, about 36 ug/g feed, about 37 ug/g feed, about 38 ug/g feed or about 40 ug/g feed. In specific embodiments, animal feed comprises about $10^5$ CFU/g *B. subtilis* 1579 and about 4 ug/g feed Quercetin, about 10 ug/g feed Apigenin, and about 36 ug/g feed.

In some embodiments, the bacterial strain composition is formulated as an animal feed with a carrier to deliver the composition to a specific region of the gastrointestinal tract of a subject. The region of the gastrointestinal tract for delivery of the bacterial strain composition can be selected based on the accumulated location of polyphenols, such as quercetin.

As provided herein, the bacterial strain composition may be combined with a base animal feed. Together, the bacterial strain composition combined with the base feed may comprise a total feed composition fed to ruminant and/or milk-producing animals according to the disclosed methods. As disclosed herein, the concentration of the bacterial strain composition in the resulting feed composition may vary. For example, in embodiments where the base feed and the bacterial strain composition are provided separately and combined by an end user, the bacterial strain concentration may be adjustable. In some examples, the concentration of the bacterial strain in the total feed composition (containing both the base feed and the phytogenic composition) may range from about $10^5$ CFU/ml to about $10^{11}$ CFU/ml, about $10^5$ CFU/ml to about $10^{10}$ CFU/ml, about $10^5$ CFU/ml to about $10^{12}$ CFU/ml, about $10^5$ CFU/ml to about $10^6$ CFU/ml, about $10^6$ CFU/ml to about $10^7$ CFU/ml, about $10^7$ CFU/ml to about $10^8$ CFU/ml, about $10^8$ CFU/ml to about $10^9$ CFU/ml, about $10^9$ CFU/ml to about $10^{10}$ CFU/ml, about $10^{10}$ CFU/ml to about $10^{11}$ CFU/ml, about $10^{11}$ CFU/ml to about $10^{12}$ CFU/ml. In other embodiments, the concentration of the bacterial strain provided herein or active variant thereof in the final animal feed composition comprises at least about $10^5$ CFU/ml, at least about $10^6$ CFU/ml, at least about $10^7$ CFU/ml, at least about $10^8$ CFU/ml, at least about $10^9$ CFU/ml, at least about $10^{10}$ CFU/ml, at least about $10^{11}$ CFU/ml, or at least about $10^{12}$ CFU/ml. In specific embodiments, the population of at least one of a bacterial strain (i.e., *B. subtilis* 1579 or an active variant of any thereof, or spores or forespores or a combination of cells, forespores and/or spores, formed from *B. subtilis* 1579, or an active variant of any thereof) in the final animal feed composition comprises a concentration of at least about $10^5$ CFU/g to about $10^{11}$ CFU/g, about $10^5$ CFU/g to about $10^{10}$ CFU/g, about $10^5$ CFU/g to about $10^{12}$ CFU/g, about $10^5$ CFU/g to about $10^6$ CFU/g, about $10^6$ CFU/g to about $10^7$ CFU/g, about $10^7$ CFU/g to about $10^8$ CFU/g, about $10^8$ CFU/g to about $10^9$ CFU/g, about $10^9$ CFU/g to about $10^{10}$ CFU/g, about $10^{10}$ CFU/g to about $10^{11}$ CFU/g, about $10^{11}$ CFU/g to about $10^{12}$ CFU/g. In other embodiments, the concentration of the bacterial strain provided herein or active variant thereof in the final animal feed composition comprises at least about $10^5$ CFU/g, at least about $10^6$ CFU/g, at least about $10^7$ CFU/g, at least about $10^8$ CFU/g, at least about $10^9$ CFU/g, at least about $10^{10}$ CFU/g, at least about $10^{11}$ CFU/g, or at least about $10^{12}$ CFU/g. the total feed composition.

In particular embodiments, the concentration of the bacterial strain composition in the total animal feed composition may be varied to target specific milk-producing animals and/or ruminants and/or specific feeding spaces. For instance, the concentration of the bacterial strain composition in the total feed composition provided to ruminants in high fence and/or pasture areas may be greater than the concentration of the bacterial strain composition in the total feed composition fed to ruminants enclosed in penned areas.

The base feed may include various feed components capable of being blended, mixed or otherwise incorporated with a bacterial strain composition. Generally, the feed components should not degrade the bacterial strain composition or decrease its effectiveness in converting polyphenols to PCA (e.g., the feed components should not counteract the effects of the bacterial strain composition). In some embodiments, the base feed may include one or more food components including but not limited to: processed grain by-products, roughage products, plant protein products, grain products, molasses products, pellet binders, vegetable oils, salts, calcium carbonate, probiotics, vitamins, minerals, and/or flavoring agents. The absolute and relative amounts of each base feed component may vary.

Embodiments may also include one or more whole grains, ground grains, or grain components. Where employed in the base feed, a whole grain, ground grain, or a grain component may be a source of carbohydrate, protein, fat, or all of these. Grain components may include bran, germ, endosperm, or portions thereof. Suitable examples of grains may include natural or genetically engineered grains including amaranth, barley, buckwheat, bulgur, corn, einkorn, farro, grano, khorasan grain, kaniwa, millet, oats, *quinoa*, rice, rye, sorghum, spelt, triticale, wheat (including durum wheat, and bread wheat including hard wheat, soft wheat, white wheat, red wheat, winter wheat, and spring wheat), and wild rice. In various embodiments, one or more sugar-containing or sugar-based components may also be included in the base feed. In some examples, sugar-containing components may include molasses, honey, sugarcane, sugar beet, fruit, fruit portions, fruit extracts, and the like. In some embodiments, the sugar containing food source is dried prior to use; for example, molasses or honey may be further dried to remove water prior to use in the base feed compositions of the invention.

In some embodiments, another suitable food component may be a whole or ground seed or an extract, or component thereof, including the oil thereof, and combinations of two or more thereof. Where employed in the base feed, a whole or ground seed or an extract, or component thereof may provide a source of carbohydrate, protein, fat, or all of these. Examples of suitable seeds may include flax seed, safflower seed, sunflower seed, rapeseed including canola, and the like. Another suitable food component may be one or more minerals. In some examples, minerals may include compounds such as monocalcium phosphate, dicalcium phosphate, calcium carbonate, sodium carbonate, sodium bicarbonate, sodium chloride, potassium chloride, potassium carbonate, potassium iodate, magnesium oxide, ferric oxide, ferrous oxide, calcium oxide, calcium hydroxide, chromic oxide, copper oxide, copper sulfate, zinc oxide, calcium chloride, copper sulfate, trace amounts of selenium, chromium, cobalt, molybdenum, manganese, fluoride, iodine, and the like. Base animal feed may also include one or more probiotic bacterial strains.

Any feedstuff disclosed herein may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In some embodiments, one or more binders, preservatives, stabilizers, emulsifiers, palatants (palatability enhancers), attractants, and combinations of two or more thereof may be suitably included in the base feed. The additives may be food safe for the selected animal. For instance, where the base feed is in a pelleted form, one or more pellet binders may be included. The pellet binders may be formulated to increase the cohesiveness of each separate base feed pellet. Flavoring agents included in the base feed may also vary in identity and/or content. In embodiments, flavoring agents may include a single flavor-enhancing component or a combination of multiple components. Examples of suitable preservatives may include one or more of sorbic acid, potassium sorbate, fumaric acid, propionic acid, and benzoic acid. Antimicrobial preservatives may include sorbic acid and its salts, benzoic acid and its salts, calcium propionate, sodium nitrite, sulfites (sulfur dioxide, sodium bisulfite, potassium hydrogen sulfite, etc.) and disodium EDTA. Antioxidants may include BHA, BHT, TBHQ and propyl gallate. Other preservatives may include ethanol and methylchloroisothiazolinone. Naturally occurring substances such as rosemary extract, hops, salt, sugar, vinegar, alcohol, diatomaceous earth and castor oil are also useful as preservatives in some embodiments of the base feed.

Examples of suitable emulsifiers may include egg yolk lecithin, mustard seed mucilage, soy lecithin, sodium stearoyl lactylate, and monoglyceride ester of diacetyl tartaric acid. Suitable stabilizers may include those that prevent undesirable interactions within the components of the base feed and/or one or more components of the phytogenic composition mixed therewith. For example, calcium sequestrants such as tetrasodium pyrophosphate may be usefully employed to prevent interaction of calcium ions with other components of the base feed and/or bacterial strain compositions, thereby maintaining stability of the feed.

In particular embodiments, a concentrate is provided having the bacterial strain composition comprising $B.$ $subtilis$ 1579 in high concentration intended for dilution prior administration to a subject. In specific embodiments a concentrated solution can comprise $B.$ $subtilis$ 1579 in a concentration of at least about $10^8$ CFU/gram to about $10^{15}$ CFU/gram, about $10^8$ CFU/gram to about $10^{12}$ CFU/gram, about $10^{10}$ CFU/gram to about $10^{12}$ CFU/gram, about $10^{10}$ CFU/gram to about $10^{15}$ CFU/gram, about $10^6$ CFU/gram to about $10^{12}$ CFU/gram, about $10^6$ CFU/gram to about $10^{10}$ CFU/gram, about $10^5$ CFU/gram to about $10^{12}$ CFU/gram, about $10^5$ CFU/gram to about $10^8$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, or about $10^{11}$ CFU/gram to about $10^{12}$ CFU/gram. In some embodiments, the concentration of the bacterial strain concentrate comprises at least about $10^8$ CFU/ml to about $10^{15}$ CFU/ml, about $10^8$ CFU/ml to about $10^{12}$ CFU/ml, about $10^{10}$ CFU/ml to about $10^{12}$ CFU/ml, about $10^{10}$ CFU/ml to about $10^{15}$ CFU/ml, about $10^6$ CFU/ml to about $10^{12}$ CFU/ml, about $10^6$ CFU/ml to about $10^{10}$ CFU/ml, about $10^5$ CFU/ml to about $10^{12}$ CFU/ml, about $10^5$ CFU/ml to about $10^8$ CFU/ml, about $10^6$ CFU/ml to about $10^7$ CFU/ml, about $10^7$ CFU/ml to about $10^8$ CFU/ml, about $10^8$ CFU/ml to about $10^9$ CFU/ml, about $10^9$ CFU/ml to about $10^{10}$ CFU/ml, about $10^{10}$ CFU/ml to about $10^{11}$ CFU/ml, or about $10^{11}$ CFU/ml to about $10^{12}$ CFU/ml. In particular embodiments, the concentration of the bacterial strain concentrate comprises at least about $10^8$ CFU/ml, at least about $10^9$ CFU/ml, at least about $10^{10}$ CFU/ml, at least about $10^{11}$ CFU/ml, at least about $10^{12}$ CFU/ml, at least about $10^{13}$ CFU/ml, at least about $10^{14}$ CFU/ml, or at least about $10^{15}$ CFU/ml.

In some embodiments, the bacterial strain composition disclosed herein is formulated as a pharmaceutical or nutraceutical composition such as a nutritional supplement and/or food additive. The pharmaceutical or nutraceutical composition may be a liquid formulation or a solid formulation. When the pharmaceutical or nutraceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip, or a film. When the pharmaceutical or nutraceutical composition is a liquid formulation it may be formulated as an oral solution, a suspension, an emulsion or syrup. The composition may further comprise a carrier material independently selected from, but not limited to, the group consisting of vegetables, lactic acid fermented foods, fermented dairy products, resistant starch, dietary fibers, carbohydrates, proteins, and glycosylated proteins. In specific embodiments, *B. subtilis* 1579 can be used as a starter culture for the fermentation of vegetable products containing quercetin and a resultant PCA fermentate can be administered to a subject. In some embodiments, the bacterial strain composition is formulated with a carrier such as guar gum to deliver the composition to a specific region of the gastrointestinal tract of a subject. The region of the gastrointestinal tract for delivery of the bacterial strain composition can be selected based on the accumulated location of polyphenols, such as quercetin.

In some embodiments, the carrier component(s) may protect the active components from degradation. In addition, or alternatively, the carrier component(s) may facilitate delivery of the active components to the gastrointestinal tract of a human or agricultural animal. In particular embodiments, the carrier components facilitate delivery of the bacterial strain composition to the gastrointestinal tract of a ruminant and/or milk-producing agricultural animal. The carrier components may be provided as a coating around the bacterial strain composition, or may be integrally mixed with the bacterial strain composition. In some examples, the carrier components may include wheat bran and/or calcium carbonate. The absolute and relative amounts of each carrier component, e.g., wheat bran or calcium carbonate, may vary in different embodiments.

As used herein, the term "pharmaceutical composition" could be formulated as a food composition, a dietary supplement, a functional food, a medical food or a nutritional product as long as the required effect is achieved, i.e. conversion of at least one polyphenol to PCA. Said food composition may be chosen from the group consisting of beverages, yogurts, juices, ice creams, breads, biscuits, crackers, cereals, health bars, spreads, and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins.

The pharmaceutical composition according to the invention, used according to the invention or produced according to the invention may also comprise other substances, such as an inert vehicle, or pharmaceutical acceptable adjuvants, carriers, preservatives etc., which are well known.

B. Active Variants of *Bacillus subtilis* 1579

Further provided are active variants of *B. subtilis* 1579. Such variants will retain the ability to convert at least one polyphenol to PCA. In some embodiments, variants will retain the ability to reduce inflammation in a subject, decrease cortisol levels in a subject, increase milk quality in milk-producing agricultural animals, and/or decrease body weight loss in agricultural animals. Active variants of *B. subtilis* 1579 provided herein include, for example, any isolate or mutant of *B. subtilis* 1579.

In specific embodiments, the bacterial strain is compatible with an antibiotic. A bacterial strain is compatible with an antibiotic when the bacterial strain is able to survive and/or reproduce in the presence of an effective amount of the antibiotic of interest. In instances where the bacterial strain is not compatible for an antibiotic of interest, if desired, methods can be undertaken to modify the bacterial strain to impart the compatibility of interest. Such methods to produce modified bacterial strains include both selection techniques and/or genetic transformation techniques.

By "modified bacterial strain" is intended a population wherein the strain has been modified (by selection and/or transformation) to have one or more additional traits of interest. In some cases, the modified bacterial strain comprises *B. subtilis* 1579, or an active variant of any thereof. A modified antibiotic-resistant strain of *B. subtilis* 1579, or an active variant thereof, has the same identification characteristics as the original sensitive strain except it is significantly more resistant to the particular antibiotic. Their identification is readily possible by comparison with characteristics of the known sensitive strain. Thus, isolated populations of modified bacterial strains are provided.

An increase in resistance to an antibiotic refers to the ability of an organism (i.e., bacterial cell or spore) to survive and reproduce following exposure to a dose of the antibiotic that would normally be lethal to the unmodified organism or would substantially reduce growth of the unmodified organism. In specific embodiments, the increase in resistance to an antibiotic is demonstrated in the presence of an effective amount of the antibiotic. Thus, active variants of the bacterial strains disclosed herein, include for example, a modified strain, such that the active variant converts at least one polyphenol to PCA and is further able to grow in the presence of at least one antibiotic.

Recombinant bacterial strains having resistance to an antibiotic can be made through genetic engineering techniques and such engineered or recombinant bacterial strains grown to produce a modified population of bacterial strains. A recombinant bacterial strain is produced by introducing polynucleotides into the bacterial host cell by transformation. Methods for transforming microorganisms are known and available in the art. See, generally, Hanahan, D. (1983) Studies on transformation of *Escherichia coli* with plasmids *J. Mol. Biol.* 166, 557-77; Seidman, C. E. (1994) In: *Current Protocols in Molecular Biology*, Ausubel, F. M. et al. eds., John Wiley and Sons, NY; Choi et al. (2006) *J. Microbiol. Methods* 64:391-397; Wang et al. 2010. *J. Chem. Technol. Biotechnol.* 85:775-778. Transformation may occur by natural uptake of naked DNA by competent cells from their environment in the laboratory. Alternatively, cells can be made competent by exposure to divalent cations under cold conditions, by electroporation, by exposure to polyethylene glycol, by treatment with fibrous nanoparticles, or other methods well known in the art.

Active variants of the various bacteria provided herein can be identified by employing, for example, methods that determine the sequence identity relatedness between the 16S ribosomal RNA, methods to identify groups of derived and functionally identical or nearly identical strains include Multi-locus sequence typing (MLST), concatenated shared genes trees, Whole Genome Alignment (WGA), MAUVE alignment, Average Nucleotide Identity, and MinHash (Mash) distance metric.

In certain embodiments, active variants of *B. subtilis* 1579 include strains that are closely related to *B. subtilis* 1579 by employing the Bishop MLST method of organism classification as defined in Bishop et al. (2009) *BMC Biology* 7(1)1741-7007-7-3. Thus, in specific embodiments, an active variant of *B. subtilis* 1579 disclosed herein includes a bacterial strain that falls within at least a 80%, 85%, 86%, 87%, 88%, 89%, 90%, 91%, 92%, 93%. 94%, 95%, 96%, 97%, 98%, 98.5%, 98.8%, 99%, 99.1%, 99.2%, 99.3%, 99.4%, 99.5%, 99.6%, 99.7%, 99.8%, or 99.9% sequence cut off employing the Bishop method of organism classification as set forth in Bishop et al. (2009) *BMC Biology* 7(1)1741-7007-7-3, which is herein incorporated by reference in its entirety. Active variants of *B. subtilis* 1579 identified by such methods will retain the ability to convert at least one polyphenol to PCA when supplied in an effective amount to a subject or composition comprising the polyphenol, such as quercetin.

In some embodiments, the active variant of *B. subtilis* 1579 disclosed herein include strains that are closely related to *B. subtilis* 1579 on the basis of the Average Nucleotide Identity (ANI) method of organism classification. ANI (see, for example, Konstantinidis, K. T., et al., (2005) *PNAS USA* 102(7):2567-72; and Richter, M., et al., (2009) PNAS 106 (45):19126-31) and variants (see, for example, Varghese, N.J., et al., *Nucleic Acids Research* (Jul. 6, 2015): gkv657) are based on summarizing the average nucleotides shared between the genomes of strains that align in WGAs. Thus, in specific embodiments, an active variant of *B. subtilis* 1579 disclosed herein includes a bacterial stain that falls within at least a 90%, 95%, 96%, 97%, 97.5%, 98%, 98.5%, 98.8%, 99%, 99.5%, or 99.8% sequence cut off employing the ANI method of organism classification as set forth in Konstantinidis, K. T., et al., (2005) *PNAS USA* 102(7):2567-72, which is herein incorporated by reference in its entirety. Active variants of *B. subtilis* 1579 identified by such methods will retain the ability to convert at least one polyphenol to PCA when supplied in an effective amount to a subject or composition comprising the polyphenol, such as quercetin.

In particular embodiments, active variants of *B. subtilis* 1579 disclosed herein include strain(s) that are closely related to *B. subtilis* 1579 on the basis of 16S rDNA sequence identity. See Stackebrandt E, et al., "Report of the ad hoc committee for the re-evaluation of the species definition in bacteriology," Int J Syst Evol Microbiol. 52(3): 1043-7 (2002) regarding use of 16S rDNA sequence identity for determining relatedness in bacteria. In an embodiment, the at least one strain is at least 95% identical to *B. subtilis* 1579 on the basis of 16S rDNA sequence identity, at least 96% identical to *B. subtilis* 1579 on the basis of 16S rDNA sequence identity, at least 97% identical to *B. subtilis* 1579 on the basis of 16S rDNA sequence identity, at least 98% to *B. subtilis* 1579 on the basis of 16S rDNA sequence identity, at least 98.5% identical to *B. subtilis* 1579 on the basis of 16S rDNA sequence identity, at least 99% identical to *B. subtilis* 1579 on the basis of 16S rDNA sequence identity, at least 99.5% identical to *B. subtilis* 1579 on the basis of 16S rDNA sequence identity, or at least 100% identical to *B. subtilis* 1579 on the basis of 16S rDNA sequence identity. Active variants of *B. subtilis* 1579 identified by such methods will retain the ability to convert at least one polyphenol to PCA when supplied in an effective amount to a subject or composition comprising the polyphenol, such as quercetin.

The MinHash (Mash) distance metric is a comparison method that defines thresholds for hierarchical classification of microorganisms at high resolution and requires few parameters and steps (Ondov et al. (2016) *Genome Biology* 17:132). Mash distance strongly corresponds to Average Nucleotide Identity method (ANI) for hierarchical classification (See, Konstantinidis, K. T. et al. (2005) PNAS USA 102(7):2567-72, herein incorporated by reference in its entirety). That is, an ANI of 97% is approximately equal to a Mash distance of 0.03, such that values put forth as useful classification thresholds in the ANI literature can be directly applied with the Mash distance.

Active variants of *B. subtilis* 1579 include strains that are closely related to *B. subtilis* 1579 on the basis of the Minhash (Mash) distance between complete genome DNA sequences. Thus, in specific embodiments, an active variant of a bacterial strain disclosed herein includes bacterial strains having a genome within a Mash distance of less than about 0.015 to the disclosed strains. In other embodiments, an active variant of a bacterial strain disclosed herein includes a distance metric of less than about 0.005, 0.010, 0.015, 0.020, 0.025, or 0.030. A genome, as it relates to the Mash distance includes both bacterial chromosomal DNA and bacterial plasmid DNA. In other embodiments, the active variant of a bacterial strain has a genome that is above a Mash distance threshold to the disclosed strains that is greater than dissimilarity caused by technical variance. In further instances, the active variant of a bacterial strain has a genome that is above a Mash distance threshold to the disclosed strains that is greater than dissimilarity caused by technical variance and has a Mash distance of less than about 0.015. In other instances, the active variant of a bacterial strain has a genome that is above a Mash distance threshold to the disclosed strains that is greater than dissimilarity caused by technical variance and has a Mash distance of less than about 0.005, 0.010, 0.015, 0.020, 0.025, or 0.030.

As used herein, "above technical variation" means above the Mash distance between two strains caused by errors in the genome assemblies provided the genomes being compared were each DNA sequenced with at least 20× coverage with the Illumina HiSeq 2500 DNA sequencing technology and the genomes are at least 99% complete with evidence for contamination of less than 2%. While 20× coverage is an art recognized term, for clarity, an example of 20× coverage is as follows: for a genome size of 5 megabases (MB), 100 MB of DNA sequencing from the given genome is required to have 20× sequencing coverage on average at each position along the genome. There are many suitable collections of marker genes to use for genome completeness calculations including the sets found in Campbell et al. (2013) *PNAS USA* 110(14):5540-45, Dupont et al. (2012) *ISMEJ* 6:1625-1628, and the CheckM framework (Parks et al. (2015) *Genome Research* 25:1043-1055); each of these references is herein incorporated in their entirety. Contamination is defined as the percentage of typically single copy marker genes that are found in multiple copies in the given genome sequence (e.g. Parks et al. (2015) *Genome Research* 25:1043-1055); each of these references is herein incorporated in their entirety. Completeness and contamination are calculated using the same collection of marker genes. Unless otherwise stated, the set of collection markers employed in the completeness and contamination assay is set forth in Campbell et al. (2013) *PNAS USA* 110(14):5540-45, herein incorporated by reference.

Exemplary steps to obtain a distance estimate between the genomes in question are as follows: (1) Genomes of sufficient quality for comparison must be produced. A genome of sufficient quality is defined as a genome assembly created with enough DNA sequence to amount to at least 20× genome coverage The genome must be at least 99% complete with contamination of less than 2% to be compared to the claimed microbe's genome. (2) Genomes are to be compared using the Minhash workflow as demonstrated in Ondov et al. (2016) *Genome Biology* 17:132, herein incorporated by reference in its entirety. Unless otherwise stated, parameters employed are as follows: "sketch" size of 1000, and "k-mer length" of 21. (3) Confirm that the Mash distance between the 2 genomes is less than 0.005, 0.010, 0.015, 0.020, 0.025, or 0.030. Active variants of *B. subtilis* 1579 identified by such methods will retain the ability to convert at least one polyphenol to PCA when supplied in an effective amount to a subject or composition comprising the polyphenol, such as quercetin.

C. Methods of Culturing *B. subtilis* 1579

Populations or cultures of *B. subtilis* 1579 can be produced by fermentation of the bacterial strain. Fermentation can be started by scaling-up a seed culture. This involves repeatedly and aseptically transferring the culture to a larger and larger volume to serve as the inoculum for the fermentation, which is carried out in large stainless steel fermentors in medium containing proteins, carbohydrates, and minerals necessary for optimal growth of the *Bacillus*. A non-limiting exemplary medium is Trypticase Soy Broth (TSB). After the bacterial inoculum is added to the fermentation vessel, the temperature and agitation are controlled to allow maximum growth. Once the culture reaches a maximum population density, the culture is harvested by separating the cells from the fermentation medium. This separation is commonly performed by centrifugation.

The concentration of the bacterial culture can be measured from any sample of fermentation broth or bacterial strain composition. A colony forming unit (CFU) is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

The various compositions and formulations disclosed herein can comprise an amount of *B. subtilis* 1579, or active variant of any thereof, or a spore or a forespore or a combination of cells, forespores or/and spores, from *B. subtilis* 1579, or an active variant thereof. Such an amount can comprise a concentration of the bacterial strain of at least about $10^4$ CFU/gram to about $10^{11}$ CFU/gram, at least about $10^5$ CFU/gram to about $10^{11}$ CFU/gram, about $10^5$ CFU/gram to about $10^{10}$ CFU/gram, about $10^5$ CFU/gram to about $10^{12}$ CFU/gram, about $10^5$ CFU/gram to about $10^6$ CFU/gram, about $10^6$ CFU/gram to about $10^7$ CFU/gram, about $10^7$ CFU/gram to about $10^8$ CFU/gram, about $10^8$ CFU/gram to about $10^9$ CFU/gram, about $10^9$ CFU/gram to about $10^{10}$ CFU/gram, about $10^{10}$ CFU/gram to about $10^{11}$ CFU/gram, or about $10^{11}$ CFU/gram to about $10^{12}$ CFU/gram. In other embodiments, the concentration of the bacterial strain comprises at least about $10^5$ CFU/gram, at least about $10^6$ CFU/gram, at least about $10^7$ CFU/gram, at least about $10^8$ CFU/gram, at least about $10^9$ CFU/gram, at least about $10^{10}$ CFU/gram, at least about $10^{11}$ CFU/gram, at least about $10^{12}$ CFU/gram, at least about $10^4$ CFU/gram.

III. Methods of Administration of *Bacillus subtilis* 1579

Methods are provided herein for increasing the production of protocatechuic acid (PCA) from at least one polyphenol with an effective amount of *B. subtilis* 1579. The methods disclosed herein can be performed in vitro, in vivo, or ex vivo. In specific embodiments, a bacterial strain composition is combined with at least one polyphenol to increase the production of PCA. As used herein an "effective amount" refers to a quantity of a bacterial strain composition comprising *B. subtilis* 1579 that increases the production of PCA from at least one polyphenol. In some embodiments and effective amount of the bacterial strain composition decreases inflammation in a subject, decreases cortisol levels, or increases milk quality and/or milk production quantity in milk-producing agricultural animals.

An effective amount of the bacterial strain composition is determined based on the intended goal. The term "unit dose" refers to a physically discrete unit suitable for use in a subject or agricultural animal, each unit containing a predetermined quantity of the bacterial strain composition calculated to produce the desired response in association with its administration, i.e., the appropriate route and treatment regimen. The quantity to be administered, both according to number of treatments and unit dose, depends on the subject or agricultural animal to be treated, the state of the subject, the environmental conditions of the subject, and the result desired. Precise amounts of the bacterial strain composition also depend on the judgment of the practitioner and are peculiar to each individual. In specific embodiments, it may be desirable to administer the *B. subtilis* 1579 bacterium in the dose range of about $10^4$ to about $10^{12}$ CFU, $10^5$ to $10^{11}$ CFU, $10^6$ to $10^{10}$ CFU, $10^8$ to $10^{10}$ CFU or $10^8$ to $10^{12}$ CFU.

As used herein, the bacterial strain composition can be used to increase the production of PCA from at least one polyphenol in any subject. By "subject" is intended animals. In specific embodiments, subjects are mammals, e.g., primates or humans. In other embodiments, subjects include domestic animals, such as a feline or canine, or agricultural animals, such as a ruminant, horse, swine, poultry, or sheep. In specific embodiments, the subject is a milk-producing agricultural animal or ruminant, such as a bovine (i.e., cow). In particular embodiments, the production of PCA from polyphenols by *B. subtilis* 1579 can be determined by measuring an end point marker after exposure of Bovine Aortic Endothelial Cells (BAEC), in vitro, to *B. subtilis* 1579. For example, an end point marker for PCA production using BAEC can be the expression of an inflammation marker, such as Cox-2.

As used herein, an "increase in" or "increasing" PCA production comprises any statistically significant increase the level of PCA when compared to an appropriate control. Such increases can include, for example, at least a 5%, 10%, 20%, 30%, 40%, 50%, 60%, 70%, 80%, 90%, 100%, 150%, 200% or greater increase in the PCA level. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the PCA level. The level of PCA can be measured in a sample taken from a subject, or measured directly in the subject. In specific embodiments, the level of PCA is measured in an intestine, colon, blood, urine, or fecal sample taken from a subject, such as a human or milk-producing agricultural animal.

In specific embodiments an increase in PCA production is measured in reference to the level of PCA in a proper control sample. As used herein a proper control includes but is not limited to, the level of PCA in a corresponding sample from a subject that was not administered the bacterial strain composition comprising *B. subtilis* 1579, the level of PCA in a sample from the subject prior to administration of the bacterial strain composition comprising *B. subtilis* 1579, or the level of PCA in a standardized sample from a subject that was not administered the bacterial strain composition comprising *B. subtilis* 1579. One of skill in the art would be able to identify proper controls in order to measure an increase in the level of PCA.

PCA can be measured by high performance liquid chromatography (HPLC). One can detect PCA using a reverse-phase gradient of mobile phase consisting of an aqueous phase such as water with or without modifiers and an organic solvent such as methanol or acetonitrile. The mobile phase is pumped across a solid phase such as C18 column. Compounds dissociating from the solid phase are detected by DAD (Diode Array Detection) or other means, at various UV wavelengths and retention times. PCA can be positively identified by comparison of the retention time and UV spectrum to authentic chemical standards. See, for example, Assefa et al. (*BMC Chem* 13:56 (2019), herein incorporated by reference.

In specific embodiments, the level of PCA from a sample collected from a subject or collected in vitro following administration of a bacterial strain composition comprising *B. subtilis* 1579 will not demonstrate an increase in PCA production. PCA produced from polyphenols can be immediately bound or utilized by the subject without providing an opportunity for accurate measurement. Thus, according to the methods and compositions disclosed herein an increase in the level of PCA can be indicated by a representative end point marker. As used herein an end point marker for an increase in the level of PCA can include a decrease in inflammation, a decrease in the expression of markers of inflammation, an increase in milk quality as measured by an increase in milk protein, increase in lactose, and/or increase in milkfat, an increase in milk production, or a decrease in weight loss in milk-producing agricultural animals when compared to a proper control.

The bacterial strain composition can be administered to a subject based on standard techniques known in the art for administration to the particular type of subject and in the environment in which the subject receives the bacterial strain composition. When administered to a human, the bacterial strain composition may be a liquid formulation or a solid formulation. When the bacterial strain composition is a solid formulation it may be formulated as a tablet, a sucking tablet, a chewing tablet, a chewing gum, a capsule, a sachet, a powder, a granule, a coated particle, a coated tablet, an enteric coated tablet, an enteric coated capsule, a melting strip or a film. When the bacterial strain composition is a liquid formulation it may be formulated as an oral solution, a suspension, an emulsion, or syrup. The bacterial strain composition can be administered by oral administration, anal administration, subcutaneous administration, transdermal administration, or any method that allows the bacterial strain, *B. subtilis* 1579, to come into contact with at least one polyphenol.

In some embodiments of the invention, the method comprises administration of multiple doses of the bacterium to a subject. The method may comprise administration of 1, 2, 3, 4, 5, 6, 7, 8, 9, 10, 15, 20, 25, 30, 35, 40, or more effective doses of a bacterial strain composition comprising *B. subtilis* 1579 as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to increase the production of PCA. It will also be appreciated that the effective amount or dosage of a bacterial strain composition may increase or decrease over the course of a particular treatment. Changes in dosage may result and become apparent from the results of diagnostic assays for detecting PCA level or end point markers known in the art and described herein.

A. Methods of Decreasing Inflammation

Compositions and methods are provided herein for decreasing inflammation in a subject by administering a bacterial strain composition comprising *B. subtilis* 1579 described elsewhere herein. In some embodiments, administration of a bacterial strain composition comprising *B. subtilis* 1579 can reduce or treat an inflammatory disease, and particularly can ameliorate the symptoms or prevent an inflammatory disease of the gastrointestinal tract, such as an inflammatory bowel disease (IBD), including, but not limited to, Crohn's disease and/or colitis (e.g., ulcerative colitis), in a subject. In some embodiments, administration of a bacterial strain composition comprising *B. subtilis* 1579 can reduce or treat an inflammatory disease, and particularly can ameliorate the symptoms or prevent a systemic inflammatory disorder outside the gastrointestinal tract, such as rheumatoid arthritis, systemic lupus erythematosus and/or multiple sclerosis, in a subject. "Treatment" is herein defined as curing, healing, alleviating, relieving, altering, remedying, ameliorating, improving, or affecting the condition or the symptoms of a subject with a gastrointestinal disorder or systemic inflammatory disorder. The systemic inflammatory disorder can be any inflammatory disorder and need not be associate with gastrointestinal inflammation. The subject to be treated can be suffering from or at risk of developing a gastrointestinal disorder, including, for example, be suffering from an inflammatory bowel disease or be at risk of developing an inflammatory bowel disease.

Administration of the bacterial strain composition can be for either a prophylactic or therapeutic purpose. By "preventing" is intended that the bacterium is provided prophylactically, i.e., the bacterium is provided in advance of any symptom. The prophylactic administration of the bacterial strain composition described herein serves to prevent or attenuate any subsequent symptom. When provided therapeutically, the bacterial strain composition is provided at (or shortly after) the onset of a symptom. The therapeutic administration of the substance may serve to attenuate any actual symptom.

In some embodiments, the reduction or decrease in inflammation may include stimulation of intestinal integrity; reduction of intestinal permeability; improvement of mucin synthesis, secretion, and/or quality; improvement of the maturation and differentiation of the intestinal epithelium; improvement of nutrient absorption; increase of the production of soluble factors that transfer antimicrobial activity; stimulation of, improvement of, or support of resistance to infection; support of cellular or humoral responses against viral or bacterial infection; increased cytotoxicity (both anti-viral and anti-tumor); support of systemic and/or mucosal vaccination responses; increase or support of cellular and/or humoral immunity; increase or support of natural immunity (including neutrophils, phagocytes, macrophages, and natural killer cell activity); increase or support of adaptive T and B cell immunity; stimulation of a helper T cell 1 (Th1) cytokine pattern (increased IL-1, IL-2, IFN-gamma, IL-12, TNF-alpha; human leukocyte antigen-Dr (HLA-Dr) expression); suppression of inflammation or production of systemic and mucosal inflammatory mediators (including cytokines and/or chemokines); reduction of sensitization by reducing total and/or allergen-specific IgE; reduction of the production of allergic cytokines; reduction of a Th2 supporting immunoglobulin profile; and combinations thereof.

As used herein, the term "anti-inflammatory cytokine" refers to a naturally occurring or recombinant protein, analog thereof or fragment thereof that elicits an anti-inflammatory response in a cell that has a receptor for that cytokine. Anti-inflammatory cytokines of the invention can be immunoregulatory molecules that control the proinflammatory cytokine response. Anti-inflammatory cytokines of the invention include interleukin (IL)-1 receptor antagonist, IL-4, IL-10, IL-11, and IL-13, IL-16, IFN-alpha, TGF-beta, G-CSF.

As used herein, the term "proinflammatory cytokine" refers to an immunoregulatory cytokine that favors inflammation. Proinflammatory cytokines of the invention include IL1-alpha, IL1-beta, TNF-alpha, IL-2, IL-3, IL-6, IL-7, IL-9, IL-12, IL-17, IL-18, LT, LIF, Oncostatin, or IFN-alpha, IFN-beta, IFN-gamma.

In some embodiments, administration of the bacterial strain composition results in an increase in anti-inflammatory cytokine production. As used herein, an "increase in" or "increasing" anti-inflammatory cytokine production comprises any statistically significant increase the anti-inflammatory cytokine level when compared to an appropriate control. Such increases can include, for example, at least a 5%, 10%, 20%, 30%, 40%, 50%, 60%, 70%, 80%, 90%, 100%, 150%, 200% or greater increase in the anti-inflammatory cytokine level. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the anti-inflammatory cytokine level. Methods to assay for the level of anti-inflammatory cytokine level, are known. See, for example, Leng S., et al. (2008) *J Gerontol A Biol Sci Med Sci* 63(8): 879-884. Methods to assay for the production of anti-inflammatory cytokines include multiplex bead assay, ELISA, ELISPOT, qPCR, and flow cytometry. See, for example, Maecker et al. (2005) *BMC Immunology* 6:13.

Methods and compositions also include those which decrease proinflammatory cytokine production, which may decrease or prevent an inflammatory response. As used herein, a decrease in the level of pro-inflammatory cytokine production comprises any statistically significant decrease in the level of pro-inflammatory cytokine production in a subject when compared to an appropriate control. Such decreases can include, for example, at least a 5%, 10%, 20%, 30%, 40%, 50%, 60%, 70%, 80%, 90%, or 100% decrease in the level of proinflammatory cytokines. Methods to assay for cytokine levels are known and include, for example Leng S., et al. (2008) *J Gerontol A Biol Sci Med Sci* 63(8): 879-884. Methods to assay for the production of pro-inflammatory cytokines include multiplex bead assay, ELISPOT and flow cytometry. See, for example, Maecker et al. (2005) *BMC Immunology* 6:13.

Inflammatory cytokine production can also be measured by assaying the ratio of anti-inflammatory cytokine production to proinflammatory cytokine production. In specific aspects, the ratio of anti-inflammatory cytokine production to proinflammatory cytokine production is increased by about 1, 2, 3, 4, 5, 6, 7, 8, 9, 10, 20, 30, 40, 50, 60, 70, 80, 90, 100, 300, 600, 900, 1000 fold or greater when compared to an appropriate control. In other aspects, the ratio of anti-inflammatory cytokine production to pro-inflammatory cytokine production is increased by about 1 to 5 fold, about 5 to 10 fold, about 10 to 20 fold, about 20 to 30 fold, about 30 to 40 fold, about 40 fold to 60 fold, about 60 fold to 80 fold, about 80 fold to about 100 fold, about 100 to 200 fold, about 200 fold to 300 fold, about 300 to 400 fold, about 400 to about 500 fold, about 500 to about 500 fold, about 500 fold to about 700 fold, about 700 fold to 800 fold, about 800 fold to about 1000 fold or greater when compared to an appropriate control. Methods to determine the ratio of anti-inflammatory cytokine production to pro-inflammatory cytokine production can be found, for example, Leng S., et al. (2008) *J Gerontol A Biol Sci Med Sci* 63(8): 879-884. Methods to assay for the production of cytokines include multiplex bead assay, ELISA, ELISPOT, qPCR, and flow cytometry. See, for example, Maecker et al. (2005) *BMC Immunology* 6:13.

In specific embodiments, administration of an effective amount of the bacterial strain composition comprising *B. subtilis* 1579 can decrease the expression of a marker of inflammation compared to a proper control. Such decreases can include, for example, at least a 5%, 10%, 20%, 30%, 40%, 50%, 60%, 70%, 80%, 90%, or 100% decrease in the level of expression of a marker of inflammation, as measured by mRNA level, qPCR, protein level, ELISA, LPS expression, or any method known in the art. In specific embodiments, the marker of inflammation comprises Cox-2, iNOS, and/or TL-6. The level of the inflammation marker can be measured as it relates to a proper control. As used herein a proper control includes but is not limited to, the expression level of a marker of inflammation in a corresponding sample from a subject that was not administered the bacterial strain composition comprising *B. subtilis* 1579, the expression level of a marker of inflammation in a sample from a subject prior to administration of the bacterial strain composition comprising *B. subtilis* 1579, or the expression level of a marker of inflammation in a standardized sample from a subject that was not administered the bacterial strain composition comprising *B. subtilis* 1579. One of skill in the art would be able to identify proper controls in order to measure an increase in the expression level of a marker of inflammation in a human subject or agricultural animal.

B. Methods for Decreasing Cortisol Level

Compositions and methods are provided herein for decreasing the cortisol levels in a subject by administering a bacterial strain composition comprising *B. subtilis* 1579 described elsewhere herein. In specific embodiments, the serum cortisol levels in a milk-producing bovine are reduced. Such reductions or decreases can include, for example, at least a 5%, 10%, 20%, 30%, 40%, 50%, 60%, 70%, 80%, 90%, or 100% decrease in the level of serum cortisol.

Elevated cortisol levels are known to suppress the immune system. Cortisol prevents glucose entry into muscle and adipose tissue and decreases activity of insulin. Moreover, cortisol has been shown to inhibit LH release in the bovine species and therefore has an effect on reproduction. Insulin availability may limit the onset of ovarian activity leading to first ovulation. Insulin is also known to reduce concentration of blood ketone bodies. The bacterial strain composition comprising *B. subtilis* 1579 disclosed herein, when used to decrease serum cortisol, in dairy cows may increase milk production or milk quality.

Cortisol level can be measured at any time following administration of the bacterial strain composition comprising *B. subtilis* 1579. For example, if the plasma cortisol level is measured on a first day, denoted day 1, subsequent measurements can be made on day 2, day 3, day 4, day 5, day 6, day 7, day 14, day 28, or daily for 1, 2 or 4 weeks. In one embodiment, determining the plasma cortisol level involves measuring a 12 hour or 24 hour AUC. Cortisol is a time-dependent measure that takes 10 to 20 min to reach peak values. As used herein a proper control includes but is not limited to, the plasma cortisol level in a corresponding sample from a subject that was not administered the bacterial strain composition comprising *B. subtilis* 1579, the plasma cortisol level in a sample from a subject prior to administration of the bacterial strain composition comprising *B. subtilis* 1579, or the plasma cortisol level in a standardized sample from a subject that was not administered the bacterial strain composition comprising *B. subtilis* 1579. One of skill in the art would be able to identify proper controls in order to measure a decrease in the plasma cortisol level.

In specific embodiments, the bacterial strain composition comprising *B. subtilis* 1579 is administered to milk-producing ruminants (i.e., dairy cows) in order to reduce the level of cortisol. Administration can be according to the methods disclosed elsewhere herein, and can include additional compositions for the reduction of cortisol level in a milk-producing agricultural animal, such as a dairy cow.

In specific embodiments, the cortisol level is decreased following administration of the bacterial strain composition disclosed herein, without a measurable increase in PCA production. As mentioned herein, PCA produced from polyphenols can be immediately bound or utilized by the subject without providing an opportunity for accurate measurement.

C. Methods for Increasing Milk Quality

Compositions and methods are provided herein for increasing milk quality or amount of milk produced by dairy cows by administering a bacterial strain composition comprising B. subtilis 1579 described elsewhere herein. As used herein, the quality of milk can be measured by measuring the protein concentration, milkfat, lactose content, and/or the proportion of milk solids). Thus, increasing the quality of milk can refer to an increase in the protein concentration, milkfat level, lactose content, level of milk solids, or any combination thereof. Such increases can include, for example, at least a 5%, 10%, 20%, 30%, 40%, 50%, 60%, 70%, 80%, 90%, 100%, 150%, 200% or greater increase in the protein concentration, milkfat level, lactose content, level of milk solids, or any combination thereof. Such increases can also include, for example, at least about a 3%-15%, 10%-25%, 20% to 35%, 30% to 45%, 40%-55%, 50%-65%, 60%-75%, 70%-85%, 80%-95%, 90%-105%, 100%-115%, 105%-120%, 115%-130%, 125%-150%, 140%-160%, 155%-500% or greater increase in the protein concentration, milkfat level, lactose content, level of milk solids, or any combination thereof.

The time period for feeding the bacterial strain composition to dairy cows is not limited, but the bacterial strain composition may be fed to dairy cows every day beginning about 3 weeks prior to the parturition of the dairy cows and continuing the feeding until 308 days after the parturition. In specific embodiments, the bacterial strain composition is fed every day beginning about one day prior to the parturition of the dairy cows and continuing the feeding until 308 days after the parturition, such as every day beginning about 35 days after the parturition of the dairy cows and continuing the feeding until 308 days after the parturition.

The protein content of milk can refer to the level of any individual milk protein or collective level of all milk proteins. In specific embodiments, the protein content or protein level of milk proteins can be determined by measuring the level of caseins or whey proteins. For example, the protein content or protein level of milk proteins can be determined by measuring the amount of ß-lactoglobulin and/or α-lactalbumin in a milk sample. The milk sample can be collected immediately following administration of the bacterial strain composition disclosed herein and subsequent measurements can be made on day 2, day 3, day 4, day 5, day 6, day 7, day 14, day 28, or daily for 1, 2 or 4 weeks. As used herein a proper control includes but is not limited to, the milk protein level in a corresponding sample that was not administered the bacterial strain composition comprising B. subtilis 1579, the milk protein level in the subject prior to administration of the bacterial strain composition comprising B. subtilis 1579, or the milk protein level in a standardized sample that was not administered the bacterial strain composition comprising B. subtilis 1579. One of skill in the art would be able to identify proper controls in order to measure an increase in the milk protein level in a milk-producing agricultural animal, such as a dairy cow.

The lactose content of milk can refer to the level of total lactose or the level of the lactose monosaccharides, glucose and galactose. In specific embodiments, the lactose content or lactose level of milk can be determined by measuring the level of total sugar or lactose in a milk sample. The milk sample can be collected immediately following administration of the bacterial strain composition disclosed herein and subsequent measurements can be made on day 2, day 3, day 4, day 5, day 6, day 7, day 14, day 28, or daily for 1, 2 or 4 weeks. As used herein a proper control includes but is not limited to, the lactose level in a corresponding sample that was not administered the bacterial strain composition comprising B. subtilis 1579, the lactose level in the subject prior to administration of the bacterial strain composition comprising B. subtilis 1579, or the lactose level in a standardized sample that was not administered the bacterial strain composition comprising B. subtilis 1579. One of skill in the art would be able to identify proper controls in order to measure an increase in the lactose level in a milk-producing agricultural animal, such as a dairy cow.

The fat content of milk can refer to the level of fat, milkfat, or butterfat. Fat content can be determined by measuring the total fat content, unsaturated fat content, saturated fat content, or any combination thereof. In specific embodiments, the fat content or fat level of milk can be determined by measuring the level of total fat a milk sample. The milk sample can be collected immediately following administration of the bacterial strain composition disclosed herein and subsequent measurements can be made on day 2, day 3, day 4, day 5, day 6, day 7, day 14, day 28, or daily for 1, 2 or 4 weeks. As used herein a proper control includes but is not limited to, the fat level in a corresponding sample that was not administered the bacterial strain composition comprising B. subtilis 1579, the fat level in the subject prior to administration of the bacterial strain composition comprising B. subtilis 1579, or the fat level in a standardized sample that was not administered the bacterial strain composition comprising B. subtilis 1579. One of skill in the art would be able to identify proper controls in order to measure an increase in the fat level in a milk-producing agricultural animal, such as a dairy cow.

The amount milk can refer to the amount of milk produced over a defined amount of time, or the amount of milk from a cow at a given time point as measured by volume or weight. In specific embodiments, the amount of milk can be determined by measuring the total volume of milk collected from a single cow or from a population of cows receiving the same treatment. The milk sample can be collected immediately following administration of the bacterial strain composition disclosed herein and subsequent measurements can be made on day 2, day 3, day 4, day 5, day 6, day 7, day 14, day 28, or daily for 1, 2 or 4 weeks. As used herein a proper control includes but is not limited to, the milk volume in a corresponding sample that was not administered the bacterial strain composition comprising B. subtilis 1579, the milk volume in the subject prior to administration of the bacterial strain composition comprising B. subtilis 1579, or the milk volume in a standardized sample that was not administered the bacterial strain composition comprising B. subtilis 1579. One of skill in the art would be able to identify proper controls in order to measure an increase in the milk volume in a milk-producing agricultural animal, such as a dairy cow.

In specific embodiments, the milk quality or milk production quantity is increased following administration of the bacterial strain composition disclosed herein, without a measurable increase in PCA production. As mentioned herein, PCA produced from polyphenols can be immediately bound or utilized by the subject without providing an opportunity for accurate measurement.

D. Methods for Decreasing Weight Loss

Compositions and methods are provided herein for decreasing weight loss in dairy cows prior to lactation, during lactation, after calving, and at any time during growth by administering a bacterial strain composition comprising *B. subtilis* 1579 described elsewhere herein. In specific embodiments, the weight loss levels in a milk-producing bovine are reduced. Such reductions or decreases can include, for example, at least a 5%, 10%, 20%, 30%, 40%, 50%, 60%, 70%, 80%, 90%, or 100% decrease in the level of serum cortisol over a defined period of time. The bacterial strain composition comprising *B. subtilis* 1579 disclosed herein, when used to decrease weight loss in dairy cows may increase milk production and/or milk quality.

Weight loss can be measured at any time following administration of the bacterial strain composition comprising *B. subtilis* 1579. For example, if the weight is measured on a first day, denoted day 1, subsequent measurements can be made on day 2, day 3, day 4, day 5, day 6, day 7, day 14, day 28, or daily for 1, 2 or 4 weeks. As used herein a proper control includes but is not limited to, the weight loss in a corresponding sample that was not administered the bacterial strain composition comprising *B. subtilis* 1579, the weight loss in the subject prior to administration of the bacterial strain composition comprising *B. subtilis* 1579, or the weight loss in a standardized sample that was not administered the bacterial strain composition comprising *B. subtilis* 1579. One of skill in the art would be able to identify proper controls in order to measure decrease in weight loss in milk-producing ruminant animal, such as a dairy cow.

EXPERIMENTAL

Example 1: Isolation and Selection of *Bacillus subtilis* Strain 1579

Aerobic spore-forming bacteria were isolated from a variety of environmental sources and stored at −80° C. Genomic DNA was isolated from each strain for genetic screening by detection of functional genes via PCR.

Isolation of spore forming strains: Samples from various environmental sources were diluted with 99 mL of sterile 0.1% peptone broth and spore-treated in a 65° C. water bath for 30 min. Serial dilutions were made and pour-plated with tempered molten Trypticase Soy Agar (TSA) (Becton, Dickenson & Company, Franklin Lakes, NJ) and incubated at 32° C. for 12-24 h. Several isolated colonies from each sample were picked and struck to TSA plates for isolation and incubated at 32° C. for 12-24 h. Isolated colonies were picked and used to inoculate 3 mL TSB (Becton, Dickenson & Company, Franklin Lakes, NJ) in a well of a 12-well culture plate (Falcon, Tewksbury, MA) and incubated at 32° C., shaking 100-125 rpm for 12-24 h. The growth culture was spun down and resuspended in 2 mL TSB with 20% glycerol. 1 mL of this mixture was frozen at −20° C. to be used for gDNA isolation, while the remaining 1 mL was frozen at −80° C. as frozen cell stock.

DNA Isolation: Genomic DNA was extracted from isolated strains using either the Roche Applied Science High Pure PCR Template Kit or the following DNA isolation protocol. Briefly, 20 µL of lysozyme (100 mg/mL) was added to 300 µL of overnight growth in TSB and incubated at 37° C. for 60 min. Then 220 µL of lysis buffer (6 M Guanidine, 20% Triton-X 100, 10 mM Tris-HCl, pH 7.5) was added and incubated at 25° C. for 15 min, and 20 µl of Protease K 800 U/ml (NEB, Ipswich, MA) was added and incubated at 55° C. for 30 min. Next, 400 µL of lysate was transferred to a Wizard SV 96 Binding Plate (Promega, Fitchburg, WI) and manufacturer's filtration instructions from Wizard SV 96 Genomic DNA Purification System was followed starting from step 3.C.4 (4/15/revision) (Promega, Fitchburg, WI).

PCR Amplifcation: Over 2000 environmental spore-forming bacteria were screened using primers QDOIB (TTGGGATCCTTATGGTTTCATCACC, SEQ ID NO: 1) and QDOIN (GATCATATGAAAACATTATGTAC, SEQ ID NO: 2) in order to detect the qdoI gene (Hirooka and Fujita, 2010). PCR reactions were set up in 25 µL volumes containing 2.5 µL 10×PCR Buffer, 1.0 50 µL mM MgCl$_2$, 0.5 µL dNTPs (10 mM each), 1.0 µL of each forward and reverse primer (10 µM each), 0.1 µL Platinum Taq (Life Technologies 10966083), 2 µL template gDNA and 18.9 µL ddH$_2$O. Touchdown thermocycler conditions started with a 4 minute denaturation at 95° C. followed by 20 cycles of denaturation at 95° C. for 30 seconds, annealing at 60° C. for 30 seconds with a decrease of 0.5° C. every cycle and extension at 72° C. for 30 seconds, followed by another 20 cycles of denaturation at 95° C. for 30 seconds, annealing at 55° C. for 30 seconds and extension at 72° C. for 30 seconds before a final extension at 72° C. for 7 minutes.

16S rRNA Sequencing: Strains selected through genetic screening were identified by sequencing the 16S rRNA gene after amplification using primers 27F-YM (5'-d{AGAGTTTGATYMTGGCTCAG}-3', SEQ ID NO: 3), and 1492R-Y (5'-d{TACCTTGTTAYGACTT}-3', SEQ ID NO: 4). PCR reactions were set up in 20 µL volumes containing 2.0 µL 10×PCR Buffer, 0.8 50 µL mM MgCl$_2$, 0.4 µL dNTPs (10 mM each), 1.6 µL of each forward and reverse primer (10 µM each), 0.08 µL Platinum Taq (Life Technologies 10966083), 2 µL template gDNA and 13.12 µL ddH$_2$O. Conditions started with a 4 minute denaturation at 95° C. followed by 35 cycles of denaturation at 95° C. for 30 seconds, annealing at 50° C. for 30 seconds and extension at 72° C. for 30 seconds before a final extension at 72° C. for 7 minutes.

Certain identified strains were positive for qdoI, and sequencing of the 16S rRNA gene indicated that most of the strains belonged to the *Bacillus subtilis* group. The qdoI fragment of *B. subtilis* 1579 was confirmed by sequencing.

Example 2: Comparison of *B. subtilis* 1579 with similar *Bacillus* Genomes

A better understanding of how an organism lives and competes in its environment can be obtained by sequencing their full genome. Since 1995, when the first complete genome sequence of the bacteria *Haemophilus influenzae* Rd KW20 was published (Fleischmann et al., 1995), sequencing of genomes has increased exponentially and powerful databases and bioinformatics programs have been developed in order to predict the functions of newly sequenced organisms. Gene function is predicted based on the genetic organization of surrounding genes, conserved protein domains within genes and alignment with genes of established function. Predicted gene functions should then be confirmed by further molecular and biochemical experiments. Comparative analysis of the draft genomes of the previously patented *Bacillus* strains (747, 1104, 1541, 1781, 1999, and 2018) to *B. subtilis* 1579 confirmed that the quercetin 2,3-dioxygenase (qdoI) gene was unique to *B. subtilis* 1579 and allowed the inventors to determine other differences in functional genes between strains.

A draft genome was obtained for *B. subtilis* 1579 to compare to previously disclosed strains by assembling paired-end Illumina reads of genomic DNA. A shotgun genomic library was prepared with the library construction kit from Kapa Biosystems with an average gDNA fragment size of 550 bp (300-1000 bp). The library was sequenced on one MiSeq flowcell for 301 cycles using a MiSeq 600-cycle sequencing kit v3 (Illumina, San Diego, CA) generating 2,720,557 paired reads.

Paired reads were uploaded to the Pathosystems Resource Integration Center (PATRIC), a Bacterial Bioinformatics Resource Center (Davis et al., 2016; Wattam et al., 2014). The reads were assembled using the auto assembly strategy that runs BayesHammer (Nikolenko et al., 2013) on short reads, followed by three assembly strategies that include Velvet (Zerbino and Birney, 2008), IDBA (Peng et al., 2010) and Spades (Bankevich et al., 2012), each of which is given an assembly score by ARAST, an in-house script. The best assembly as selected by PATRIC, was then submitted to the Genome Annotation Service that uses the RAST tool kit (RASTtk) (Brettin et al., 2015) to annotate genomic features.

The contigs of the draft genome were aligned and ordered with Mauve genome alignment software (Darling et al., 2010) against a fully sequenced genome and then concatenated with a 100 Ns demarcating the contig boundaries. The concatenated draft genome was then compared to previously assembled genomes using various tools in Geneious 8.1.7 (Kearse et al., 2012) and PATRIC (Wattam et al., 2014).

The draft genomes were between 3.91 and 4.11 Mb in size with 3894 to 4180 predicted genes as shown below is Table 1.

TABLE 1

General characteristics of the draft genomes obtained for the *Bacillus subtilis* strains

|  | Available *Bacillus subtilis* Strains | | | | | | Current Disclosure |
| --- | --- | --- | --- | --- | --- | --- | --- |
|  | 747 | 1104 | 1541 | 1781 | 1999 | 2018 | 1579 |
| Size (Mb) | 4.04 | 4.11 | 3.91 | 4.05 | 3.92 | 3.96 | 3.99 |
| Number of Contigs | 38 | 42 | 32 | 36 | 32 | 41 | 19 |
| % GC | 46.2 | 46.1 | 46.4 | 46.2 | 46.5 | 46.5 | 43.8 |
| Annotated Genes | 4065 | 4180 | 3894 | 4066 | 3953 | 3894 | 4159 |
| Genes with predicted functions | 2986 | 3068 | 2938 | 2987 | 2971 | 2938 | 3563 |
| Hypothetical genes | 934 | 960 | 810 | 933 | 804 | 810 | 596 |

A phylogenetic tree based upon similarities and differences in the draft genomes was created by MAUVE alignment, which indicates that the previously disclosed strains are more similar to each other than to *B. subtilis* 1579 (FIG. 1).

Figure 2:
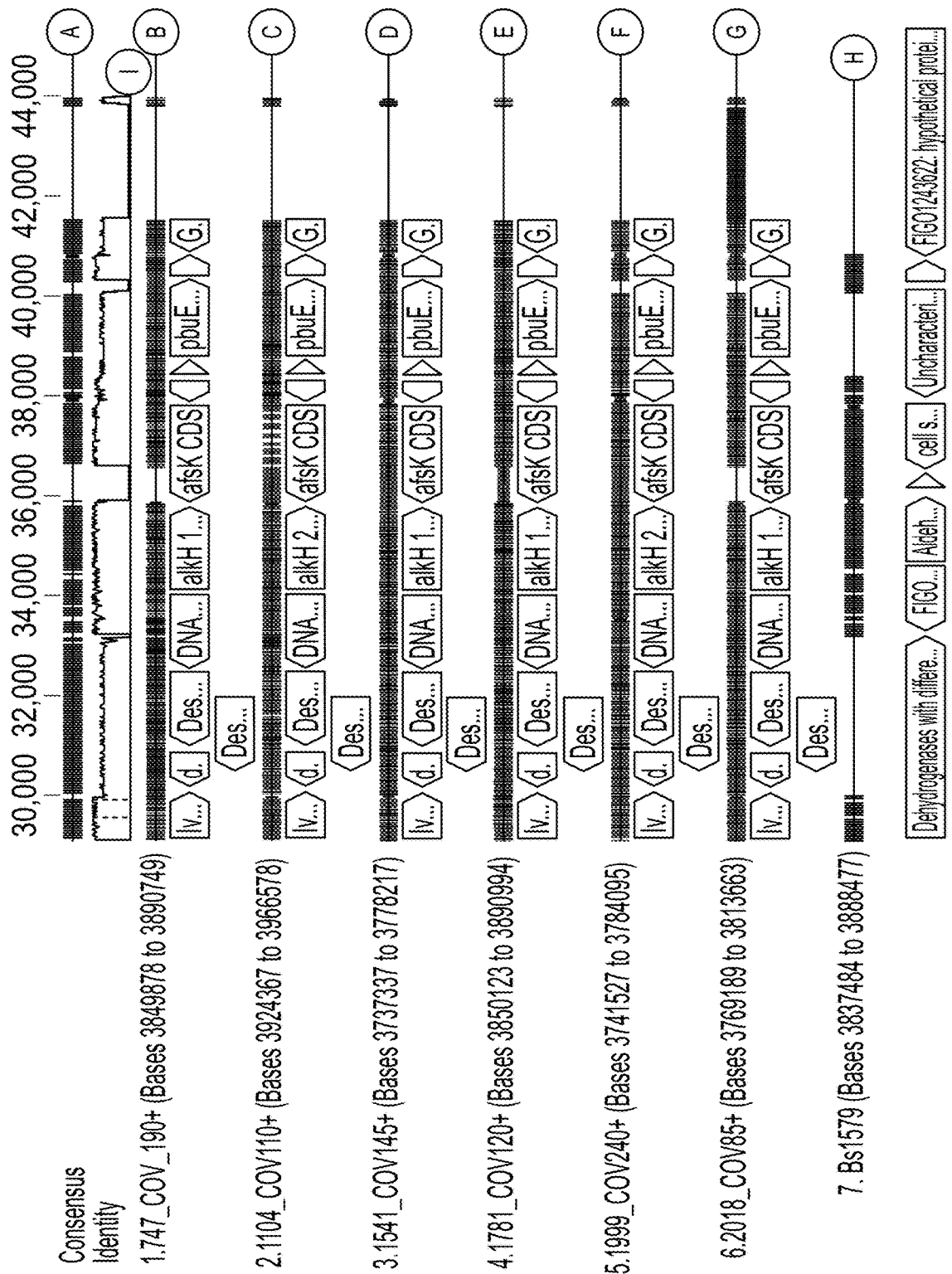
FIG. 2 shows a Mauve alignment of a co-linear block indicating that the qdoI gene (grey) and neighboring genes are present in *B. subtilis* 1579, but absent in *Bacillus* strains 747, 1104, 1541, 1781, 1999 and 2018.
Figure 2:
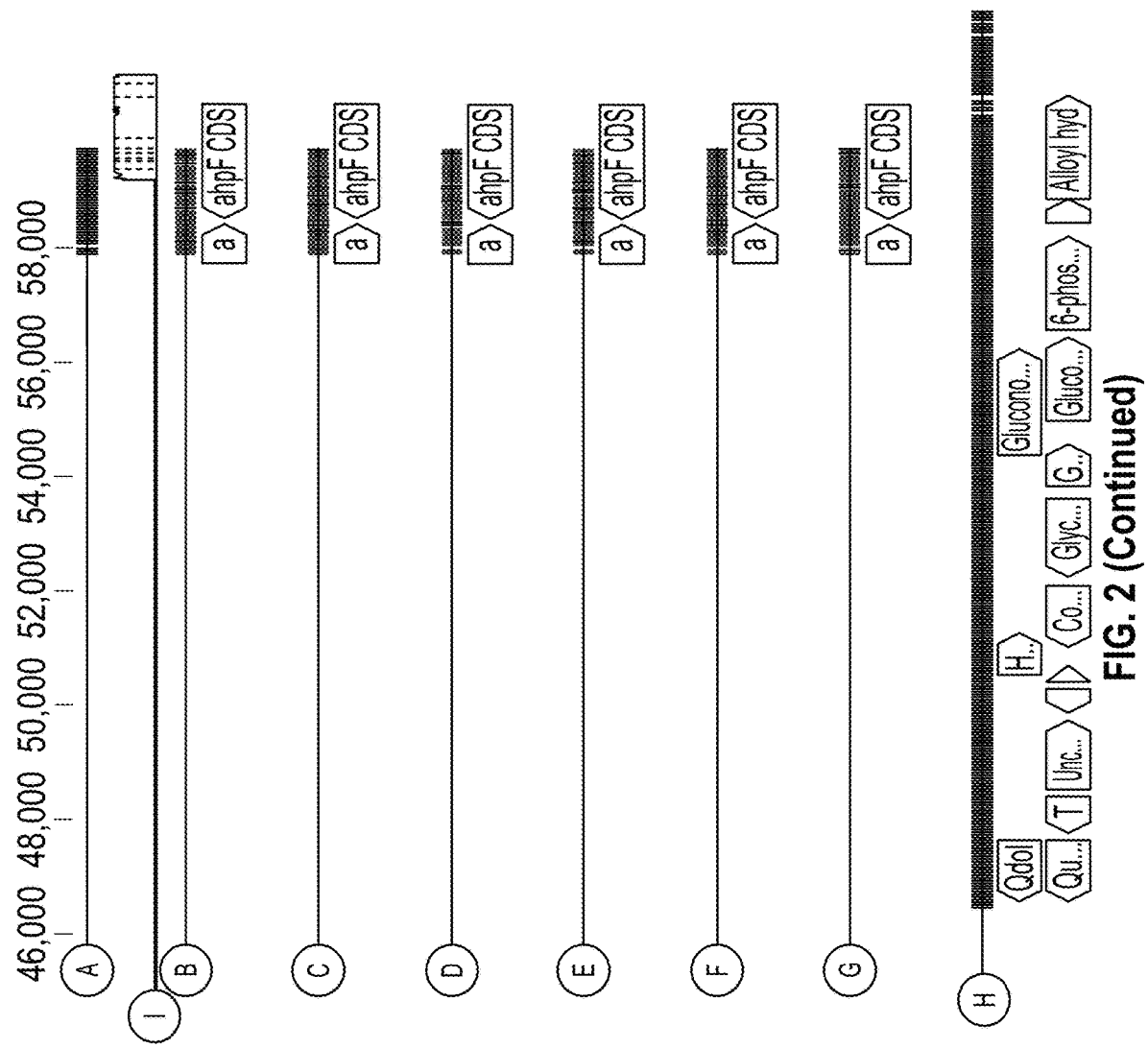

As shown in FIG. 2, quercetin 2,3-dioxygenase (EC 1.13.11.24) gene and neighboring genes were only present in *B. subtilis* 1579 as shown in the Mauve alignment.

Conclusion. An in depth comparison of the genome of the *B. subtilis* 1579, according to one embodiment of the present invention, to previously patented strains indicates that there are multiple genetic differences between all the strains. Functionally and genetically, the *B. subtilis* 1579, according to one embodiment of the present invention, is different than similar *Bacillus* strains previously disclosed.

Example 3: Safety and Antibiotic Resistance of *B. subtilis* 1579

Introduction. Antibiotic resistant bacteria are of concern in public health when they cause infections in humans as they are resistant to treatment. Bacteria may be intrinsically resistant to certain antibiotics due to factors such as cell wall and membrane structures preventing access to the cell and efflux pumps removing the antibiotic from the cell. Resistance to antibiotics can also occur when the antibiotic target is modified and the antibiotic cannot bind to the target to inhibit growth. The concern for public health is the transfer and acquisition of entire plasmids and other mobile elements encoding resistance factors.

Full genome sequences need to be available for bacterial strains to be commercialized to determine whether they contain transmissible resistance genes or whether measurable resistance to any antibiotic is intrinsic resistance due to, for instance, efflux genes. There are additional benefits to having the full genome sequence of strains; for example, we can confirm the absence of toxin genes, such as emetic toxin.

Methods. National Antimicrobial Resistance Monitoring System (NARMS) panel screening: *B. subtilis* 1579 was grown overnight at 37° C. and the resulting culture transferred into a 15 mL conical tube and spun down at 4700 rpm for 10 min. A sterile swab was used to take a portion of the pellet and resuspended in sterile ddH2O tubes; a 0.5 McFarland standard was used to determine the optimal dilution. 15 microliters of the ddH2O was transferred into the 5 mL tubes of Mueller-Hinton broth and the mixture was vortexed and poured into a sterile boat. A p200 multi-channel pipette was used to transfer 50 microliters into each well of the SENSITITRE 96-well microtiter plate (CMV3AGPF) plate (FIG. 3) and sealed. The plates were incubated at 37° C. overnight. The plates were removed at 18 hours and each well was given a result of either positive or negative depending on if there was any growth in the well.

Screening for transmissible antibiotic resistance genes in the genome: There are several searchable databases available to determine the presence of antibiotic resistance genes in sequenced strains:

1. The Antibiotic Resistance Genes Database (ARDB) contains representatives of experimentally confirmed antibiotic resistance genes as well as drug targets in which mutations have been shown to confer resistance (Liu and Pop, 2009). This database is not currently maintained and was last updated on Jul. 3, 2009.
2. The Comprehensive Antibiotic Resistance Database (CARD; card.mcmaster.ca/) is a curated collection of known resistance genes that is updated monthly. (McArthur et al., 2013).
3. ResFinder (cge.cbs.dtu.dk/services/ResFinder/) identifies acquired antimicrobial resistance genes in total or partial sequenced isolates of bacteria (Zankari et al., 2012). This database only covers horizontally acquired resistance genes and does not include resistance mediated by mutations found in housekeeping genes.

Emetic Toxin screening: *B. subtilis* 1579 was screened for the Tecra *Bacillus cereus* emetic toxin using the (3M, Maplewood, MN) Bacillus Diarrhoeal Enterotoxin Visual Immunoassay kit.

Results. The Minimum Inhibitory Concentrations (MIC) for the antibiotics in the National Antimicrobial Resistance Monitoring System (NARMS) panel for *B. subtilis* 1579 are indicated in Table 3. The potential transmissible antibiotic resistance genes detected in the draft genome by the three databases, ARDB; CARD and ResFinder, are shown in Table 4.

TABLE 3

Minimum Inhibitory Concentrations (MIC) for the antibiotics in the National Antimicrobial Resistance Monitoring System (NARMS) panel for *B. subtilis* 1579 tested in duplicate.

| | | | | MIC Interpretive Criteria (pg/mL) | | |
|---|---|---|---|---|---|---|
| Class | Agent | 1579a | 1579b | Suscept. | Inter. | Resist. |
| Aminoglycosides | | | | | | |
| | Streptomycin | 1024 R | 512 S | ≤512 | N/A | ≥1024 |
| | Kanamycin | 128 S | 1024 R | ≤512 | N/A | ≥1024 |
| | Gentamycin[1] | 128 S | 128 S | ≤500 | N/A | ≥500 |
| Cyclic Lipopepides | | | | | | |
| | Daptomycin | 0.5 S | 1 S | ≤4 | N/A | ≥8 |
| Fluoroquinolone | | | | | | |
| | Ciprofloxacin | 0.25 S | 0.12 S | ≤1 | 2 | ≥4 |
| Glycopeptides | | | | | | |
| | Tigercycline | 0.12 S | 0.12 S | ≤0.25 | N/A | |
| | Vancomycin | 2 S | 2 S | ≤4 | 8-16 | ≥32 |
| Lincosamides | | | | | | |
| | Lincomycin | ≥8 R | ≥8 R | ≤2 | 4 | ≥8 |
| Macrolides | | | | | | |
| | Tylosin tartrate | 2* S | 0.5 S | ≤ 8 | 16 | ≥32 |
| | Erythromycin | 1 I | 0.5 S | ≤0.5 | 1-4 | ≥8 |
| Nitrofurans | | | | | | |
| | Nitrofurantoin | 16 S | 16 S | ≤32 | 64 | ≥128 |
| Oxazolidinone | | | | | | |
| | Linezolide | 4 I | 8 R | ≤2 | 4 | ≥8 |
| Penicillins | | | | | | |
| | Penicillin | 1 S | 0.5 S | ≤2 | N/A | ≥8 |
| Phenicols | | | | | | |
| | Chloramphenicol | 16 I | 8 S | ≤8 | 16 | ≥32 |

TABLE 3-continued Minimum Inhibitory Concentrations (MIC) for the antibiotics in the National
Antimicrobial Resistance Monitoring System (NARMS) panel for *B. subtilis*
1579 tested in duplicate.

| | | | | MIC Interpretive Criteria (µg/mL) | | |
|---|---|---|---|---|---|---|
| Class | Agent | 1579a | 1579b | Suscept. | Inter. | Resist. |
| Streptogramins | | | | | | |
| Quinupristin/dalfopristin | | 4 | 32 | ≤1 | 2 | ≥4 |
| | | R | R | | | |
| Tetracyclines | | | | | | |
| Tetracycline | | 2 | 1 | ≤4 | 8 | ≥16 |
| | | S | S | | | |

S = susceptible, I = intermediate, R = resistant. Susceptible/intermediate/resistant breakpoints were determined in accordance with the Clinical Laboratory Standards Institute's 3rd ed. M45 guidelines for *Bacillus* spp. when possible (CLSI, 2010). All other interpretations were conducted using NARMS interpretive criteria for *Enterococcus* species.

TABLE 4

Putative antibiotic resistance genes detected in the draft genome of *B. subtilis* 1579
by the ResFinder, ARDB and CARD database. None of these genes were determined to confer
resistance and/or be associated with a mobile element and are therefore not considered to be
transmissible.

| Database | Gene | Product | Resistance | Query Coverage | Identity |
|---|---|---|---|---|---|
| ARDB | ykkC | Efflux pump | Multiple | 100 | 100 |
| ARDB | ykkD | Efflux pump | Multiple | 100 | 99 |
| ARDB | EC 3.6.1.27 | Peptidoglycan biosynthesis | Bacitracin | 100 | 99 |
| ARDB | fosB | Glutathione transferase | Fosfomycin | 93 | 97 |
| ARDB | MFS transporter | Efflux pump | Multiple | 100 | 99 |
| ARDB | norA | Efflux pump | Multiple | 100 | 100 |
| ARDB | lmrB | Efflux pump | Multiple | 100 | 100 |
| ARDB | bmr3 | Efflux pump | Multiple | 100 | 99 |
| ARDB | tmrB | | Tunicamycin | 100 | 98 |
| CARD | EC 2.7.7.6 | RNA polymerase | Multiple | 96 | 81 |
| CARD | Tu | Translation elongation factor | Multiple | 100 | 86 |
| ResFinder | aadK | Aminoglycoside 6-adenylyltransferase (EC 2.7.7.-) | Aminoglycosides | 100 | 99 |

Discussion. Certain bacteria have an innate ability to resist the antimicrobial action of particular antibiotics. Intrinsic resistance can be due to features of the bacteria that prevent the antibiotic from entering the cell or binding to its target. Antibiotics can also be exported from the cell by efflux pumps that actively transport metabolites with a similar chemical structure or by enzymes that inactivate the antibiotic.

Six of the nine potential antibiotic resistance genes detected by ARDB are efflux pumps that when expressed may actively transport antibiotics out of the cell, but are chromosomal genes required for normal cell function and not associated with mobile elements. The other three genes are also chromosomally encoded, not associated with mobile elements, and may result in resistance to bacitracin, fosfomycin and tunicamycin. None of these compounds are considered a threat to public health and are therefore not included in the NARMS panel.

The two genes detected by CARD are essential housekeeping genes that may be the target of antibiotics. Mutations in these genes confer resistance by preventing antibiotic binding. Again, these genes are chromosomally encoded and not associated with mobile elements. The single gene detected by ResFinder is a chromosomally encoded gene that confers intrinsic resistance by modifying the antibiotic. This gene may be responsible for the inconsistent results obtained for the aminoglycosides in the NARMS panel, but is not associated with mobile elements.

Although none of the genes detected by the databases are of concern there are still antibiotics to which *B. subtilis* 1579 is resistant. The antibiotics for which complete or partial resistance was determined for *B. subtilis* 1579 belong to the aminoglycosides, lincosamides, macrolides, oxazolidinones, phenicols and streptogramins. What these antibiotics have in common is that they all bind to the ribosome and thereby interfere with protein synthesis essential for bacterial metabolism and growth. Aminoglycosides bind to the 30S ribosomal subunit and interfere with peptide elongation resulting in inaccurate translation and/or truncated proteins. The aadK gene inactivating the aminoglycosides may account for the variable resistance measured. The other four classes all bind to the 50S ribosomal unit specifically the 23S rRNA peptidyl transferase center and inhibit protein translation. *B. subtilis* 1579 contains a gene that methylates the 23S rRNA at positon A2503. The function of this gene [23S rRNA (adenine(2503)-C(2))-methyltransferase & tRNA (adenine(37)-C(2))-methyltransferase (EC 2.1.1.192)] is to refine ribosome functions and loss of the gene results in reduced proofreading of proteins. Methylation at this site impedes binding of the four classes of antibiotics and strains are therefore less susceptible to the antibiotics.

Conclusion. No transmissible antibiotic resistance genes or toxin genes were detected in *B. subtilis* 1579.

Example 4: Functional Biotransformation of Quercetin to Protocatechuic Acid by *B. subtilis* 1579

While small quantities of protocatechuic acid are found naturally in plants, polyphenols, the precursors of phenolic acids, are found in high quantities in plants, fruits and seeds such as onion, raspberry, buckwheat, cottonseed, alfalfa, and clover. When these polyphenols are metabolized by specific bacteria, higher levels of PCA are released from the diet. This phenolic acid had greater bioavailability and tissue distribution than the parent polyphenol yet still exerts anti-inflammatory and other effects, for instance, through down regulation of NF-κB and MAPK transduction pathways (Wang et al., 2010), the central regulators of inflammation. This decrease in signaling can dampen inflammation by decreasing cytokine and cyclooxygenase (COX2) production, and cellular signaling (Farombi et al., 2016). Small phenolic compounds such as aspirin are well known to decrease inflammation through inhibition of COX-2 signaling (Hsu et al., 2009). Research by the inventors identified *B. subtilis* 1579, a unique bacterial strain capable of metabolizing certain polyphenols to PCA in order to help modulate the immune system and benefit animal health and performance.

The ability to increase the concentration of PCA in the body as a result of more efficient utilization of dietary sources can have important benefits in human and animal health.

In vivo rodent studies were conducted to substantiate the effect of *B. subtilis* 1579 on PCA production from a high polyphenol containing diet. Mice were maintained on standard rodent chow supplemented with 0.1% rutin. The diet for mice in the experimental group was supplemented with *B. subtilis* 1579 spores supplied in the feed, while control mice received only 0.1% rutin supplemented feed. After 7 days, the gastrointestinal and fecal contents were collected, polyphenols and metabolites were extracted by liquid-liquid extraction and the levels of PCA and rutin in the feces were assessed by Ultra High Performance Liquid Chromatography. Detection and quantification analyses were performed using a Shimadzu Nexera 2 UHPLC system equipped with a photodiode array detector, with UV chromatograms recorded at 260 (PCA) and 360 nM (rutin and quercetin). Samples were standardized by addition of an internal standard of catechin to the sample prior to extraction. Analytes were identified by retention time and UV spectra compared against authentic standards.

As described in FIGS. 4A-4B, treatment with *B. subtilis* 1579 resulted in a significant increase in PCA production in the feces (FIG. 4A) and cecum (FIG. 4B) of treated animals compared to animals without *B. subtilis* 1579. Moreover, as described in FIGS. 4C-4D, a concomitant decrease of rutin present in the feces (FIG. 4C) and cecum (FIG. 4D) of *B. subtilis* 1579 treated mice, but not control mice, confirms the utilization of rutin by *B. subtilis* 1579 to produce PCA.

Mice maintained on a diet including 0.1% quercetin and *B. subtilis* 1579 demonstrated higher concentrations of the metabolite protocatechuic acid (PCA) in the intestinal contents and feces, in comparison to mice maintained on the same diet alone, without *B. subtilis* 1579. *B. subtilis* 1579 can convert polyphenols such as rutin to the bioactive metabolite PCA. Consistent with rutin acting as the source of PCA there is a trend toward less rutin in *B. subtilis* 1579 treated animal feces with a significant decrease in rutin in the cecum.

Example 5: Anti-Inflammatory Activity of Protocatechuic Acid

Controlling stress and inflammation is essential in maintaining health. The inflammatory process requires energy utilization and releases a host of inflammatory mediators. This inflammation, if left unchecked often leads to secondary tissue damage, increased body temperature and heart rate, and decreased feed intake and milk production. Various plant derived compounds are well known to influence immune development and oxidative status. These phytochemicals bolster the immune system and provide antioxidant relief by directly absorbing reactive oxidants as well as activating the body's inherent antioxidant systems while modulating the immune system. Phenolic acids, such as protocatechuic acid (PCA), exert their protective effects by scavenging free radicals and, perhaps more importantly, by directly binding cellular targets (Masella et al., 2012). This direct mode of action allows PCA to inhibit key inflammatory enzymes and modulate cellular receptors leading to regulation of growth and immune responses (Quideau et al., 2011).

To determine potential mode of action of PCA, in vitro studies were performed using Bovine Aortic Endothelial Cells (BAEC). Stress was induced in mammalian endothelial cells using a lipopolysaccharide (LPS) model, which causes an inflammatory response through inflammatory cytokine, NO and prostaglandin release. After 6 hours, cells were lysed and cellular RNA was recovered using Direct-zol RNA MiniPrep Plus kit (Zymo Research) following the manufacturer's instructions. RNA was converted to cDNA using the QuantiNova Reverse Transcription Kit (Qiagen). Gene expression was then quantified using the QuantiTect SYBR Green PCR kit with primers specific for inflammatory markers. Inducible nitric oxide expression was screened using primers iNOSF (GGCTACGGAACTGGACAT-CAAC, SEQ ID NO: 7) and iNOSR (CTCAGGGATTCTG-GAGACG, SEQ ID NO: 8), Cyclo-oxygenase 2 primers, COX2F (TCCTGAAACCCACTCCCAACA, SEQ ID NO: 9) and COX2R (TGGGCAGTCATCAGGCACAG, SEQ ID NO: 10), and Interleukin-6 primers IL6F (ATGACTTCTGCTTTCCCTACCC, SEQ ID NO: 11) and IL6R (GCTGCTTTCACACTCATCATTC, SEQ ID NO: 12) compared against the house keeping gene GAPDH, primers GAPDH-F (GTCTTCACTACCATGGAGAAGG, SEQ ID NO: 13) and GAPDH-R (TCATG-GATGACCTTGGCCAG, SEQ ID NO: 14). Quantitative PCR reactions were set up in 20 μl volumes as per the manufacturer's recommendations (Qiagen). Thermocycler conditions started with a 15 min denaturation at 95° C. followed by 40 cycles of denaturation at 95° C. for 15 seconds, annealing at 60° C. for 30 seconds and extension at 60° C. for 30 seconds before a melt curve.

As described in FIGS. 5A-5B, both Cox-2 and iNOS gene expression is decreased with 1 g/ml and 10 g/ml PCA treatment. An analysis of inflammatory gene expression using real-time quantitative PCR demonstrated that PCA decreased COX-2 expression in bovine cells during inflammatory stress (FIG. 5A). Similarly, LPS expression of iNOS, typically associated with inflammation, was decreased in PCA treated, LPS stimulated cells (FIG. 5B). Finally, as described in FIG. 5C, IL-6, an important mediator of inflammation and fever, is dose dependently decreased with 1 g/ml and 10 g/ml PCA (FIG. 5C).

As described in FIGS. 5A-5C, in vitro studies using mammalian bovine aortic endothelial cells stimulated with LPS and treated with varying concentrations of protocatechuic acid demonstrated the ability of protocatechuic acid to inhibit inflammatory markers.

Example 6: *B. subtilis* 1579 Quercetin Biotransformation Trial in Humans

Polyphenols, such as quercetin, catechins and anthocyanins are present in the human diet, primarily in fruits and vegetables. When these polyphenols are metabolized by intestinal bacteria, higher levels of PCA are unlocked from the diet. This phenolic acid has increased bioavailability and tissue distribution compared to the parent polyphenol, yet still exerts antioxidant, anti-inflammatory and other effects, for instance, through down regulation of NF-κB and MAPK transduction pathways (Wang et al., 2010), the central regulators of inflammation. This decrease in signaling can dampen inflammation by decreasing cytokine and cyclooxygenase (COX2) production, and cellular signaling. In vitro studies support a role for PCA in preventing neurodegenerative disorders through anticytotoxic and antiapoptotic effects (Zhang et al., 2009, 2010; Kaewmool et al., 2020). Research by the inventors has identified *Bacillus* strain 1579, a unique bacterial strain capable of metabolizing certain polyphenols to PCA in order to help modulate the immune system and benefit human health.

The ability to increase the concentration of PCA in the body as a result of more efficient utilization of dietary sources can have important benefits in human and animal health, partially through the decrease in inflammatory markers such as IL-6 and the downstream C-reactive protein. Small phenolic compounds such as aspirin are well known to decrease inflammation through inhibition of COX-2 signaling (Hsu et al., 2009).

A study in human participants was conducted by the inventors to substantiate the effect of *B. subtilis* 1579 on PCA production from oral supplementation with a quercetin, in humans. Participants (n=3) were asked to minimize or refrain from foods high in quercetin for 24 hours leading up to urine and fecal sample collections. 24 hours prior to sample collection, a 500 mg capsule of quercetin (quercetin dihydrate) was taken orally. On day 0, urine and fecal samples were collected. Following the initial sample (T0), participants began oral dosing of *B. subtilis* 1579. Oral dosing continued daily for 10 days. On day 9, participants again received a 500 mg tablet of quercetin along with the final *B. subtilis* 1579 dose. On day 10, final samples were collected.

Biotransformation: Fecal samples were extracted by liquid-liquid extraction and the levels of PCA in the feces were assessed by Ultra High-Performance Liquid Chromatography. Detection and quantification analyses were performed using a Shimadzu Nexera 2 UHPLC system equipped with a photodiode array detector, with UV chromatograms recorded at 260 (PCA). Analytes were identified by retention time and UV spectra compared against authentic standards.

Inflammation: To assess the effects of *B. subtilis* 1579 on systemic inflammation, C-reactive protein was quantified in urine in the same study. Urine samples from day 0 and day 10 were assessed for C-reactive protein using an ELISA according to the manufacturer's instructions (Sigma Aldrich, RAB0096).

Figure 6:
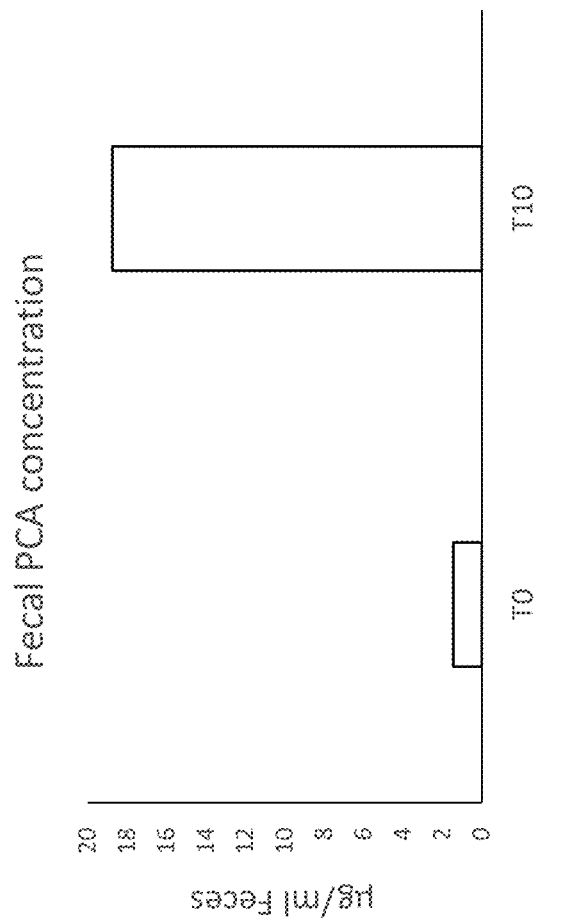
FIG. 6 is a graph depicting the production of PCA in fecal samples at day 0 and after day 10 of treatment with *B. subtilis* 1579 in combination with a 500 mg dose of quercetin.
Figure 7:
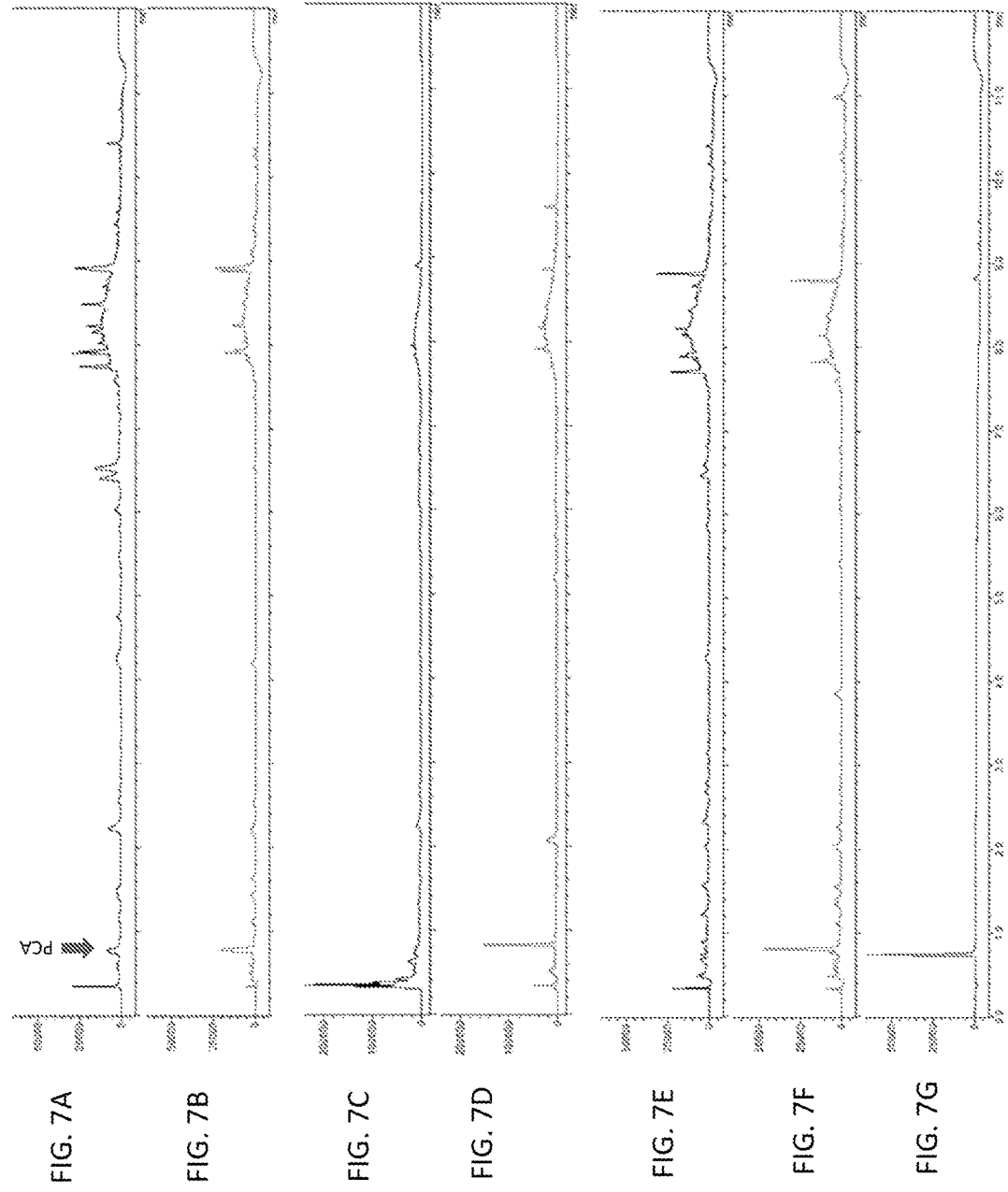
FIGS. 7A-7G provide chromatographs showing PCA production after *B. subtilis* 1579 treatment. The chromatographs are from fecal samples of participants treated with quercetin alone or after treatment with *B. subtilis* 1579 and quercetin.

Treatment with *B. subtilis* 1579 and quercetin resulted in an increase in PCA production in the feces at day 10 compared to fecal samples at day 0 with quercetin alone (FIG. 6A). The treatment with *B. subtilis* 1579 on quercetin supplementation increased the occurrence of PCA in the fecal samples. The participants demonstrated a 2.5, 23.3 and 26.8-fold increase in PCA production from day 0 to day 10 (FIGS. 7A-7F).

Figure 8:
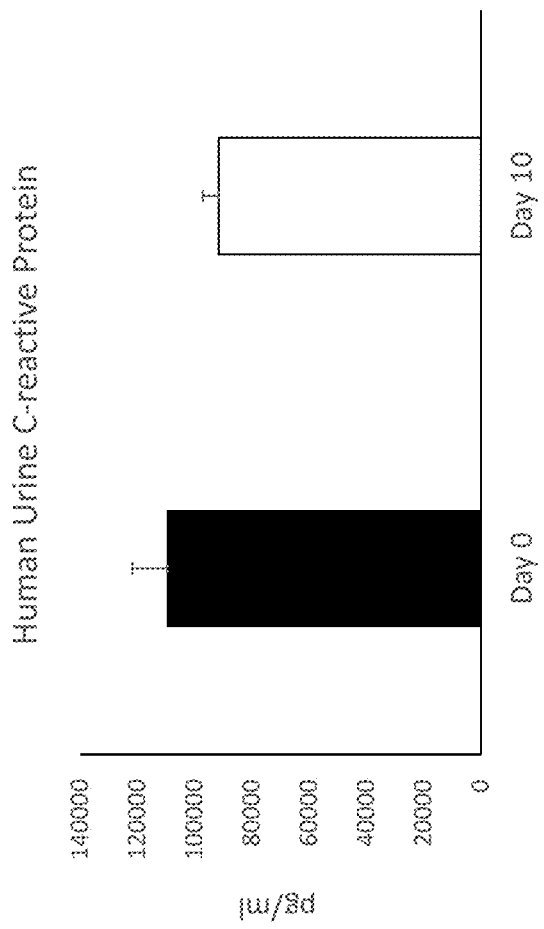
FIG. 8 is a graph showing urinary C-reactive protein levels in human participants treated with quercetin alone (day 0) or after 10 days of treatment with *B. subtilis* 1579 and quercetin.

Treatment with *B. subtilis* 1579 and quercetin demonstrated a decrease in the amount of C-reactive protein in the urine on day 10 compared to day 0 (quercetin alone). The treatment with *B. subtilis* 1579 along with quercetin supplementation decreased the levels of C-reactive protein in all participants, with an average of a 15% decrease compared to day 0 (FIG. 8; $p<0.10$).

As described in FIGS. 6, 7A-7G and 8, human participants supplemented with quercetin and *B. subtilis* 1579 demonstrated higher concentrations of the metabolite protocatechuic acid (PCA) in the feces, after supplementation of *B. subtilis* 1579. Consistent with an increase in PCA, participants demonstrated lower concentrations of the systemic inflammatory marker C-reactive protein after supplementation of *B. subtilis* 1579. Hence, *B. subtilis* 1579 converts polyphenols such as quercetin to the bioactive metabolite PCA and demonstrates a concomitant decrease in inflammatory markers.

Example 7: In vivo actions of *B. subtilis* 1579 in heifers

Small phenols and hydroxybenzoic acids such as aspirin and protocatechuic acid have been shown to provide beneficial effects for milk production in cows (Farney et al., 2013). Control of inflammation in animals after parturition can have beneficial effects on overall animal health. Protocatechuic acid (PCA) has anti-inflammatory effects resulting in a decrease in inflammatory markers and stress. Growing evidence demonstrates that dietary phytochemicals exert a variety of beneficial effects on modulating inflammation in the body. Recently it has become clear that many of these phytochemicals become more effective when metabolized by specific bacteria present in healthy individuals. The processing of these phytochemicals to smaller metabolites aids in bioavailability, tissue distribution and targeting to specific molecular pathways. We have isolated a unique strain of *B. subtilis* capable of biotransforming polyphenols present in cow rations into the anti-inflammatory compound, PCA. As described in Example 4 hereinabove, preliminary studies demonstrated that mice that were fed a high polyphenol diet in the presence of *B. subtilis* 1579 produced higher concentrations of PCA than animals without the bacteria.

Eight heifers were fed a diet high in quercetin. For the first 24 hours, animals were confined to tie stalls to monitor feed intake, after this the animals were kept in a holding pen away from the heard. Four of the animals were inoculated with a single dose of *B. subtilis* 1579 in maltodextrin at $1\times10^9$ CFU and maintained on a daily dose $1\times10^5$ CFU in feed for 7 days. Blood samples were taken on day 7 after beginning treatment by tail bleed. Immediately after collection, the samples were centrifuged to remove blood cells and the resulting serum was collected and frozen at −20 C. Cortisol levels were assessed in serum on day 7 by ELISA (LsBIO, Seattle WA, LS-F10124) as per the manufacturer's instructions. Production data, milk production and milk components were recorded.

Figure 9A:
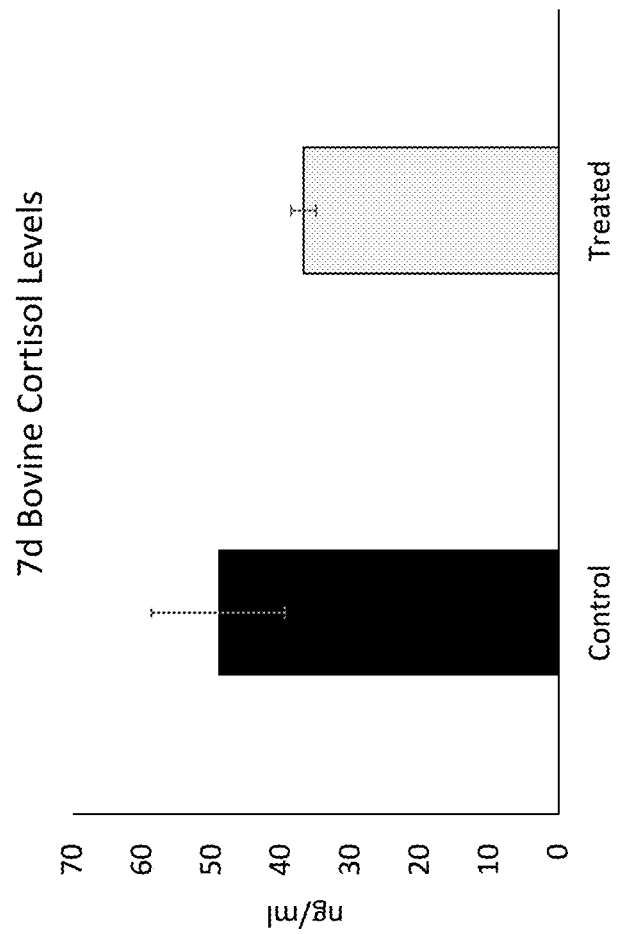
FIGS. 9A-9B provide graphs showing the impact of *B. subtilis* 1579 on stress levels in heifers.
Figure 9B:
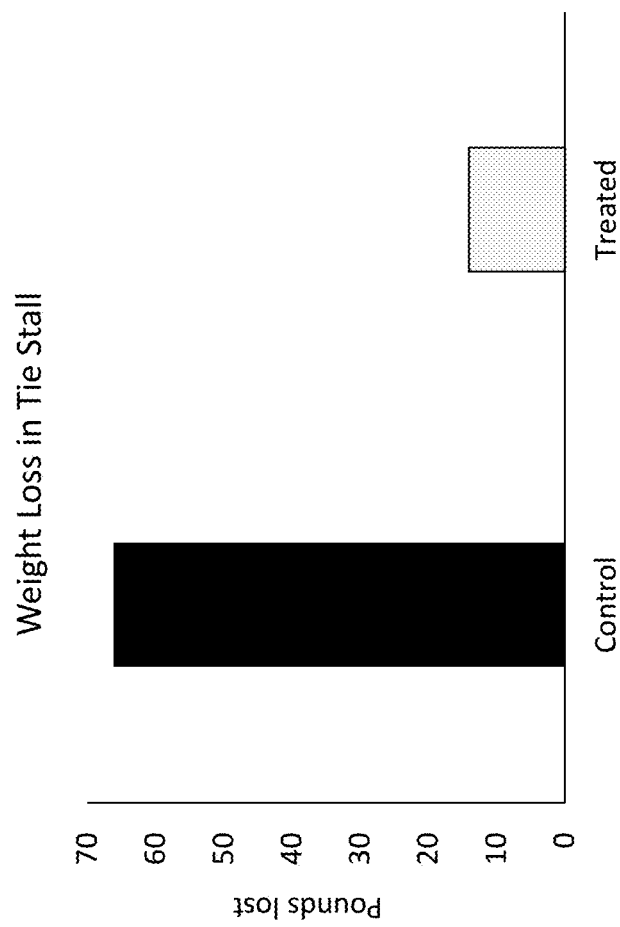
Figure 10A:
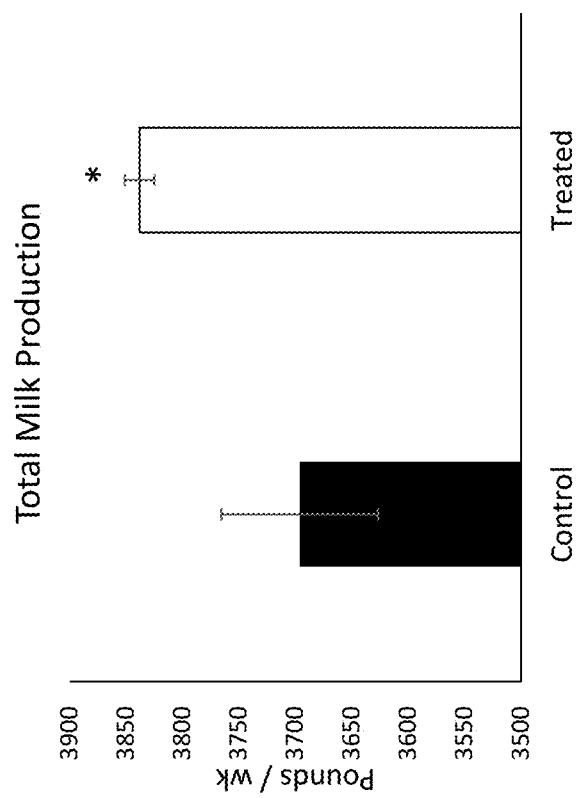
FIGS. 10A-10E provide graphs showing the impact of *B. subtilis* 1579 on milk production and milk components in heifers.
Figure 10B:
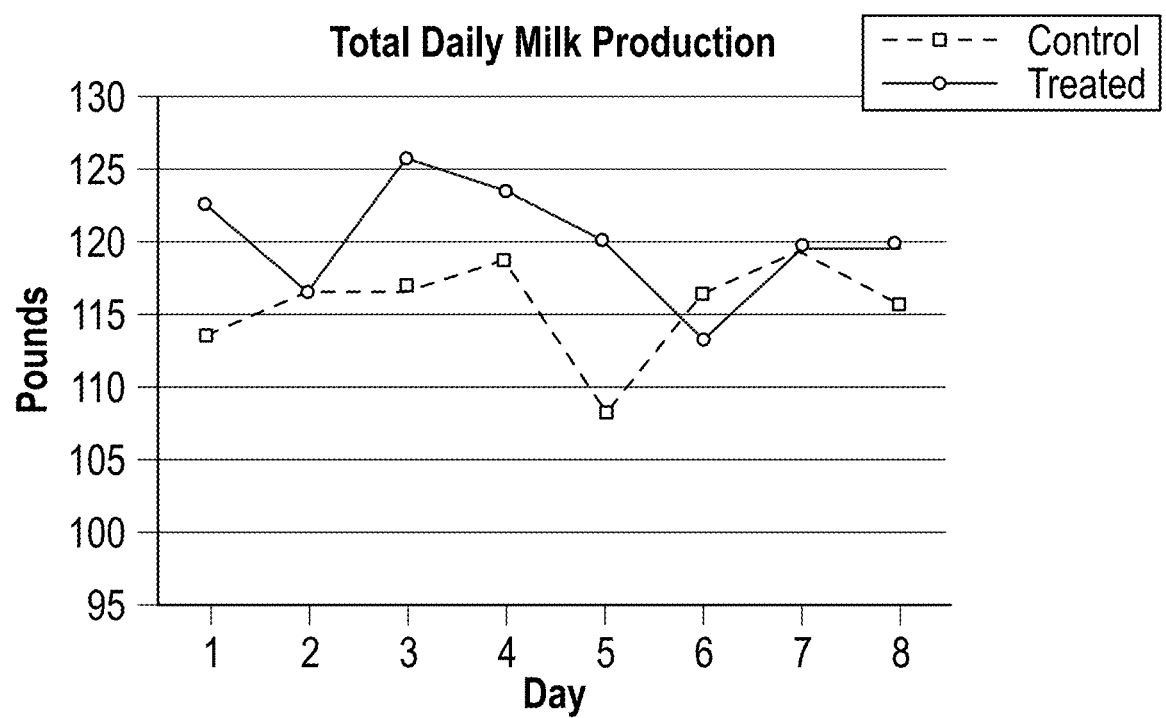
Figure 10C:
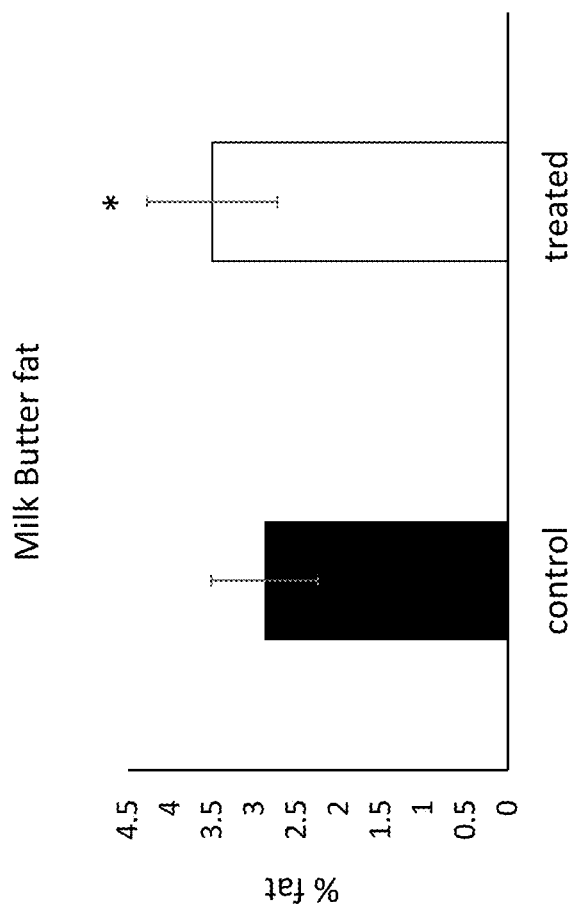
Figure 10D:
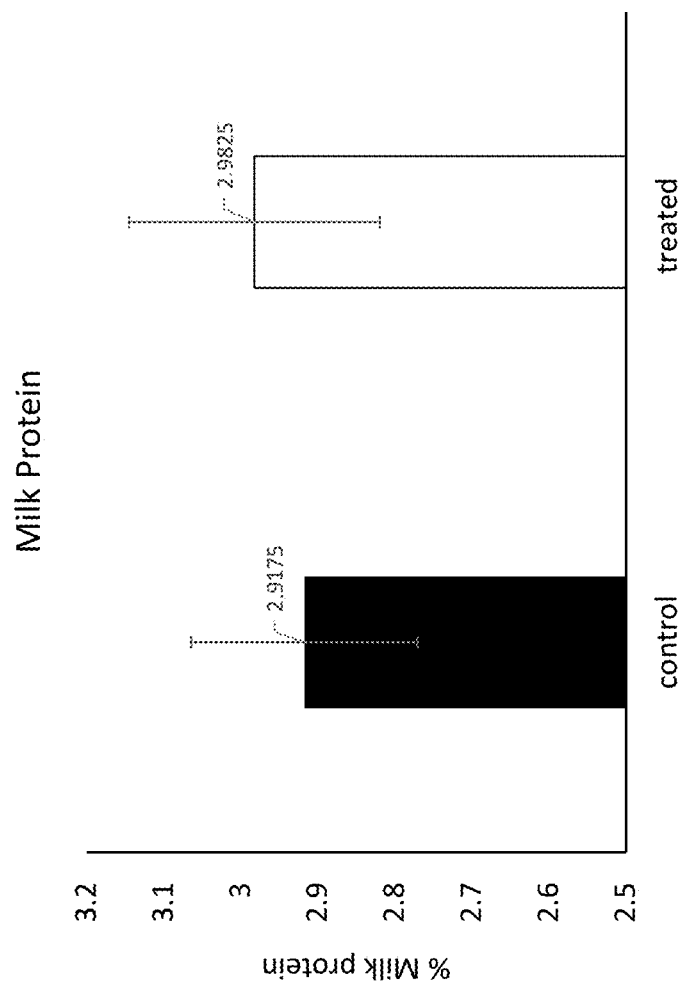
Figure 10E:
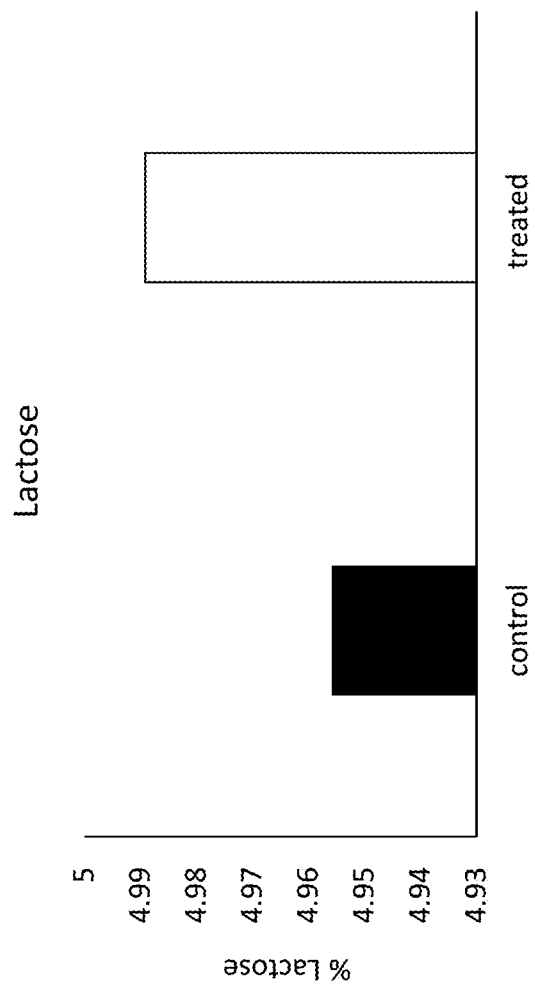

Treatment with *Bacillus* 1579 in the feed of animals resulted in a decrease in the stress hormone, cortisol at day 7 compared to animal that received control feed (FIG. 9A; $p<0.1$). This decrease in cortisol was consistent with the tendency for *Bacillus* 1579 treated animals to lose less body weight because of tie stall stress (FIG. 9B, $p=0.17$) compared to control animals. Furthermore, total milk production per week (FIG. 10A; $p<0.03$) and total daily milk production (FIG. 10B) was elevated in the *Bacillus* 1579 treated animals compared to the untreated controls, with a statistically significant increase in milk butterfat ($p<0.05$; FIG. 10C). Also, as described in FIGS. 10D-10E, other components of milk, such as milk protein (FIG. 10D) and lactose (FIG. 10E), were higher in the treated animals, although the increase was not statistically significant.

Example 8: *B. subtilis* 1579 Quercetin Biotransformation Trial in Cows

An in vivo cow study was conducted to the kinetics of PCA production by *B. subtilis* 1579. Cows were maintained on standard ration containing added cottonseed (3%) as a dietary source of polyphenol. The diet for cows in the experimental group was supplemented with *B. subtilis* 1579 spores supplied in the feed. For the quercetin biotransformation trial, 8 cows were randomly divided among two treatments: 4 control; 4 inoculated with *B. subtilis* 1579 (bolus $1\times10^9$ cfu). $1\times10^5$ CFU was maintained on standard ration feed supplemented with cottonseed for 7 days. The feed used in the study contained: Quercetin=4.23 ug/g feed; Apigenin=10.23 ug/g feed; Luteolin=35.57 ug/g feed. All cows were 80-120 days in milk. Blood was collected at $T_0$, $T_{30min}$, and hourly for 24 hours, and Day 7 for measurement of metabolites and protein. Blood was collected at $T_0$, $T_{Hr6}$, $T_{Hr9}$, and $T_{Hr12}$, and Day 7 for RNA measurements. Urine was also collected for metabolite measurement.

Metabolites were extracted using SPE (Solid Phase Extraction) and detection performed by UHPLC. RNA was isolated using Qiagen Quantinova RT kit. qPCR was used to for detection (SYBR) of IL-6, TNFα, and COX2. Cortisol was detected with a protein ELISA (R&D Systems).

No PCA or quercetin was detected in the feces, urine or blood from the study. PCA produced was likely immediately utilized or bound up in the body (plasma, organs, upper GI tract). Strong interactions with albumen can bind up metabolites.

Inflammatory markers were unchanged between control and treatment group; however, no inflammation was detected by qPCR in the control group. All markers showed ΔCt values >32 cycles suggesting low activity.

That which is claimed:

1. A method of increasing the production of protocatechuic acid (PCA) from at least one polyphenol, said method comprising combining said at least one polyphenol with an effective amount of a bacterial strain composition comprising:
   a) *Bacillus subtilis* 1579 deposited under accession number NRRL B-67952; or
   b) a combination of cells with forespores and/or spores of *Bacillus subtilis* 1579 deposited under accession number NRRL B-67952,
   wherein said effective amount of said bacterial strain composition comprises $10^5$ CFU/gram to $10^{12}$ CFU/gram or at $10^5$ CFU/ml to $10^{12}$ CFU/ml of *Bacillus subtilis* 1579.

2. The method of claim 1, wherein said at least one polyphenol comprises a flavonoid polyphenol.

3. The method of claim 2, wherein said flavonoid polyphenol comprises quercetin, apigenin, luteolin, anthocyanin, and/or rutin.

4. The method of claim 2, wherein said flavonoid polyphenol comprises quercetin glycoside, apigenin glycoside, luteolin glycoside, anthocyanin glycoside, and/or rutin glycoside.

5. The method of claim 1, wherein said bacterial strain composition comprises a cell paste or lyophilized powder.

6. The method of claim 1, wherein production of PCA is increased by at least 10% compared to a level of PCA produced without combining said at least one polyphenol with the bacterial strain composition.

\* \* \* \* \*